(12) United States Patent
Sakon et al.

(10) Patent No.: US 6,627,732 B1
(45) Date of Patent: Sep. 30, 2003

(54) GLUTATHIONE DERIVATIVES AND THEIR DOSAGE FORMS

(75) Inventors: Kiyoyuki Sakon, Hino (JP); Yoshimitsu Naniwa, Hino (JP); Mitsuru Kobayashi, Hino (JP); Daishiro Miura, Hino (JP); Hiroshi Imai, Hino (JP); Atsushi Imaizumi, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/673,449

(22) PCT Filed: Apr. 16, 1999

(86) PCT No.: PCT/JP99/02044

§ 371 (c)(1),
(2), (4) Date: Oct. 16, 2000

(87) PCT Pub. No.: WO99/54346

PCT Pub. Date: Oct. 28, 1999

(30) Foreign Application Priority Data

Apr. 16, 1998 (JP) ............................. 10-106359

(51) Int. Cl.[7] ................................. C07K 5/08
(52) U.S. Cl. .......................... 530/331; 514/18; 514/19; 562/557; 562/573
(58) Field of Search ..................... 514/19, 18; 562/557, 562/573; 530/331

(56) References Cited

FOREIGN PATENT DOCUMENTS

| WO | 95 05863 A | 3/1995 |
|----|------------|--------|
| WO | 96/40205 | 12/1996 |
| WO | 99 37802 A | 7/1999 |
| WO | 00/44366 | 8/2000 |

OTHER PUBLICATIONS

Matthew H. Lyttle et al., "Isozyme–specific glutathione–S–transferase inhibitors: design and synthesis" Journal of Medicinal Chemistry (1994) vol. 37, No. 1, p. 189–194.

Paul J. Ciaccio et al., "Modulation of detoxification gene expression in human HT29 cells by glutathione–S–transferase inhibitors" Molecular Pharmacology (1995) vol. 48, No. 4, p. 639–647.

Ryan T. Koehler et al., "Ligand–based protein alignment and isozyme specificity of glutathione S–transferase inhibitors" Proteins Structuro, Function and Genetics (1997), vol. 28, No. 2, p. 202–216.

*Primary Examiner*—Christopher S. F. Low
*Assistant Examiner*—David Lukton
(74) *Attorney, Agent, or Firm*—Sughrue Mion, PLLC

(57) ABSTRACT

The present invention provides a glutathione derivative having a dramatically enhanced hematopoiesis promoting effect in the living body represented by the formula (I):

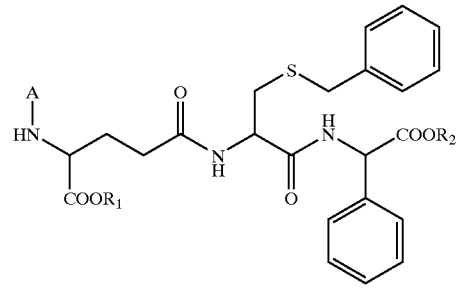

where A represents H or a C1–C20 acyl group; $R_1$ represents a C1–C26 alkyl group or a C3–C26 alkenyl group; and $R_2$ represents H, a C1–C26 alkyl group or a C3–C26 alkyl group, with the proviso that compounds are excluded in which $R_1$ is a C1–C10 alkyl group or a C3–C10 alkenyl group, and simultaneously $R_2$ is H, a C1–C10 alkyl group or a C3–C10 alkenyl group. The present invention also provides a salt of the glutathione derivative, or a colloidal composition that enables the safe and effective development of the effects of the glutathione derivative in the living body.

15 Claims, 14 Drawing Sheets

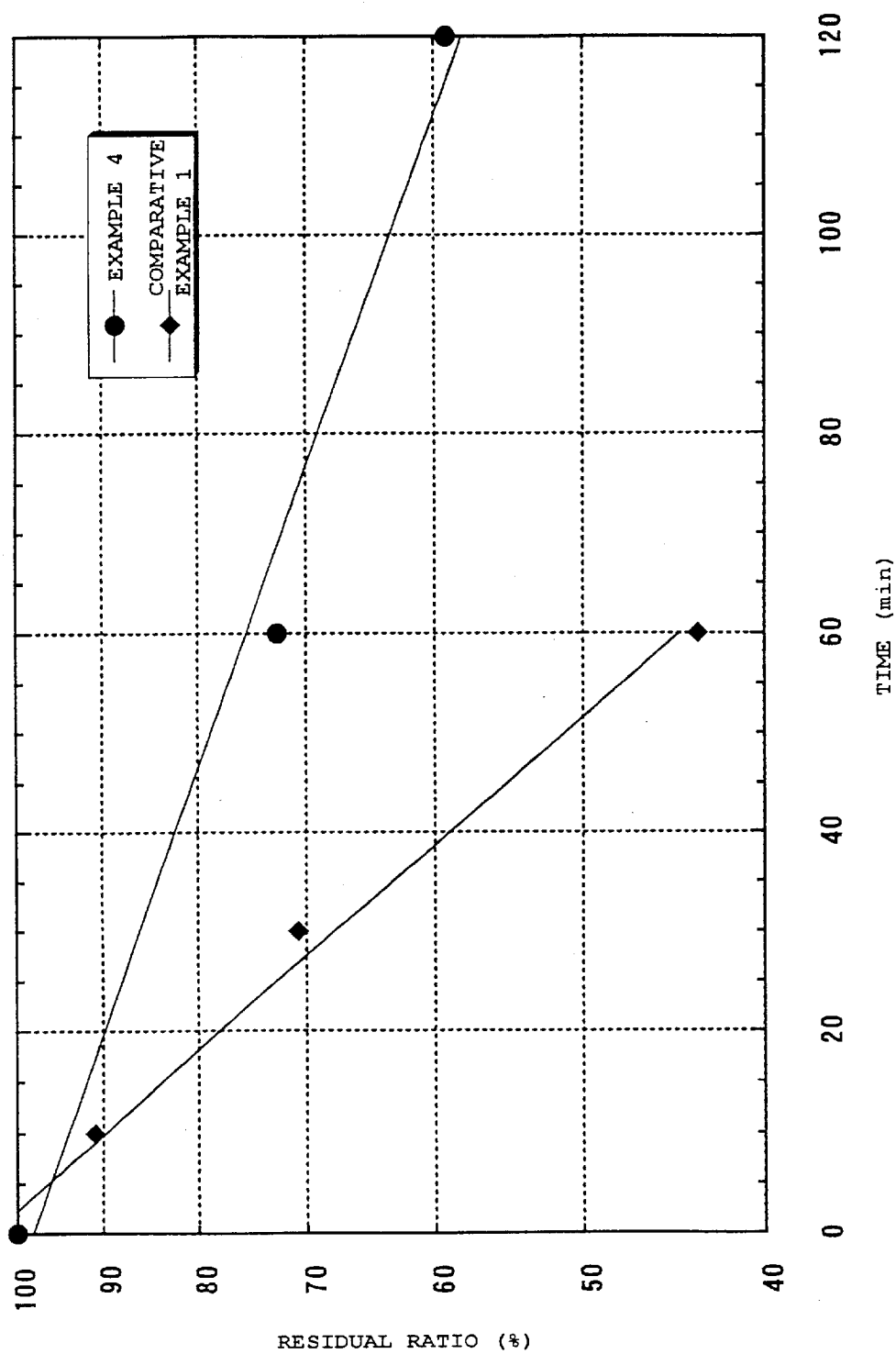

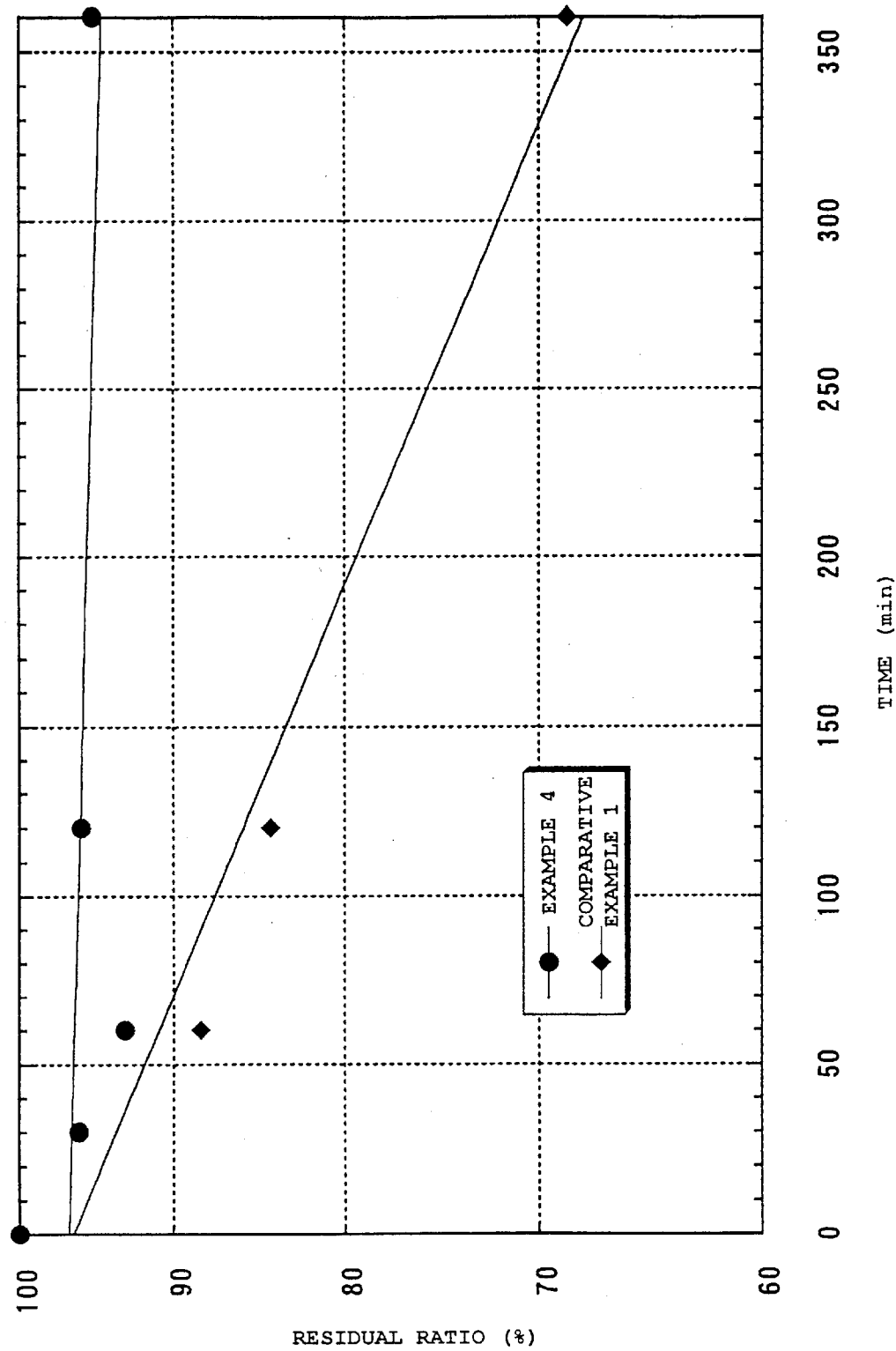

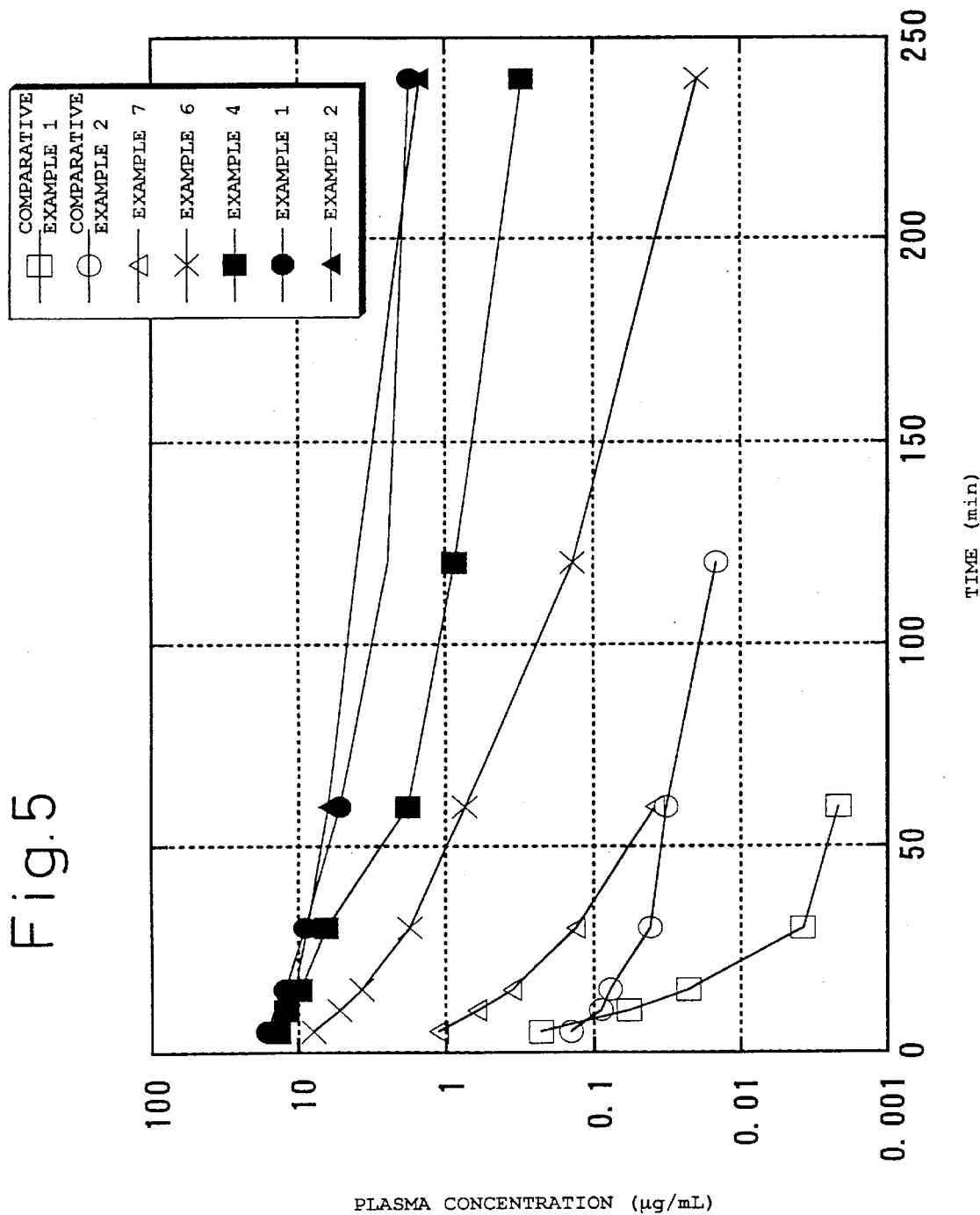

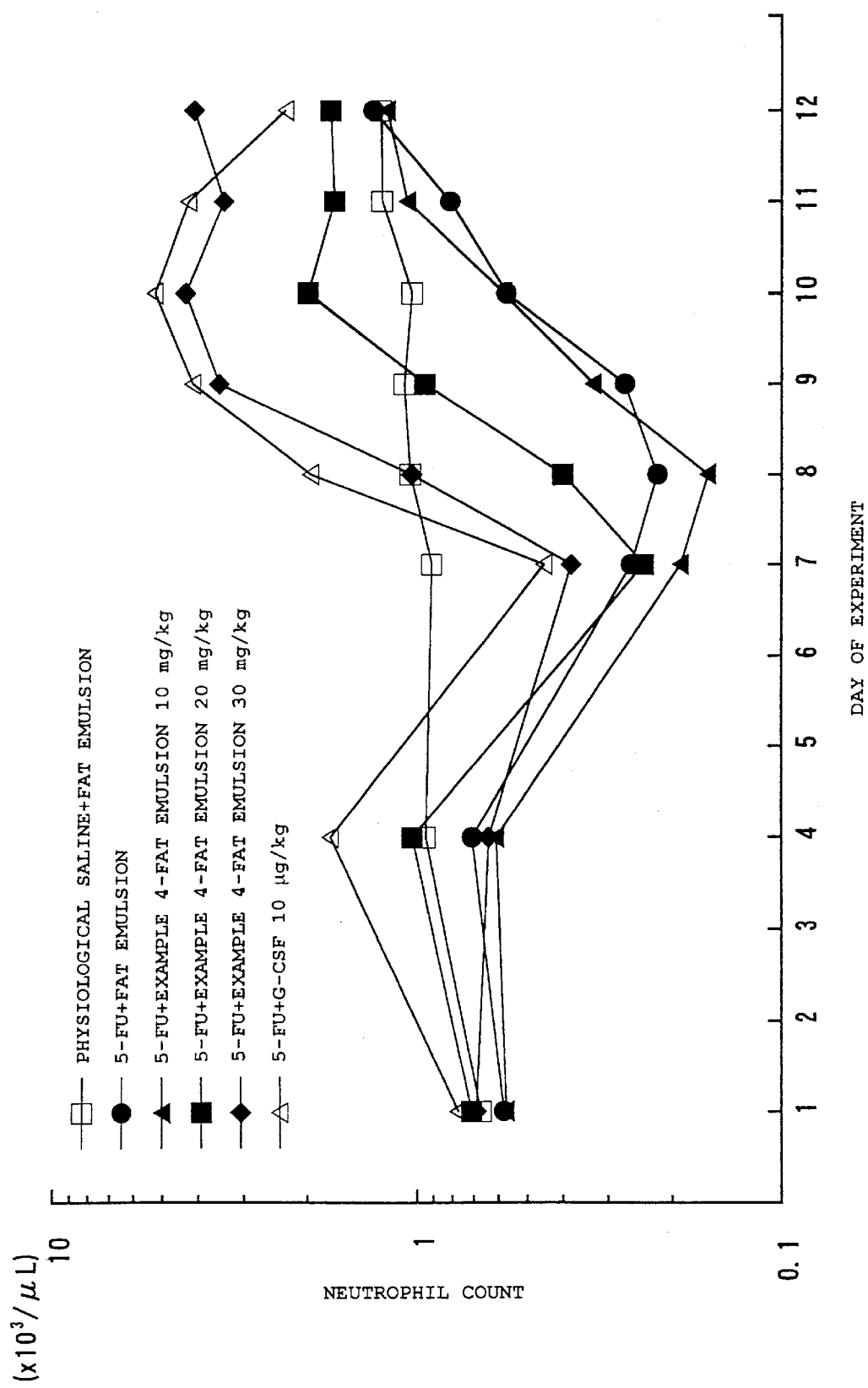

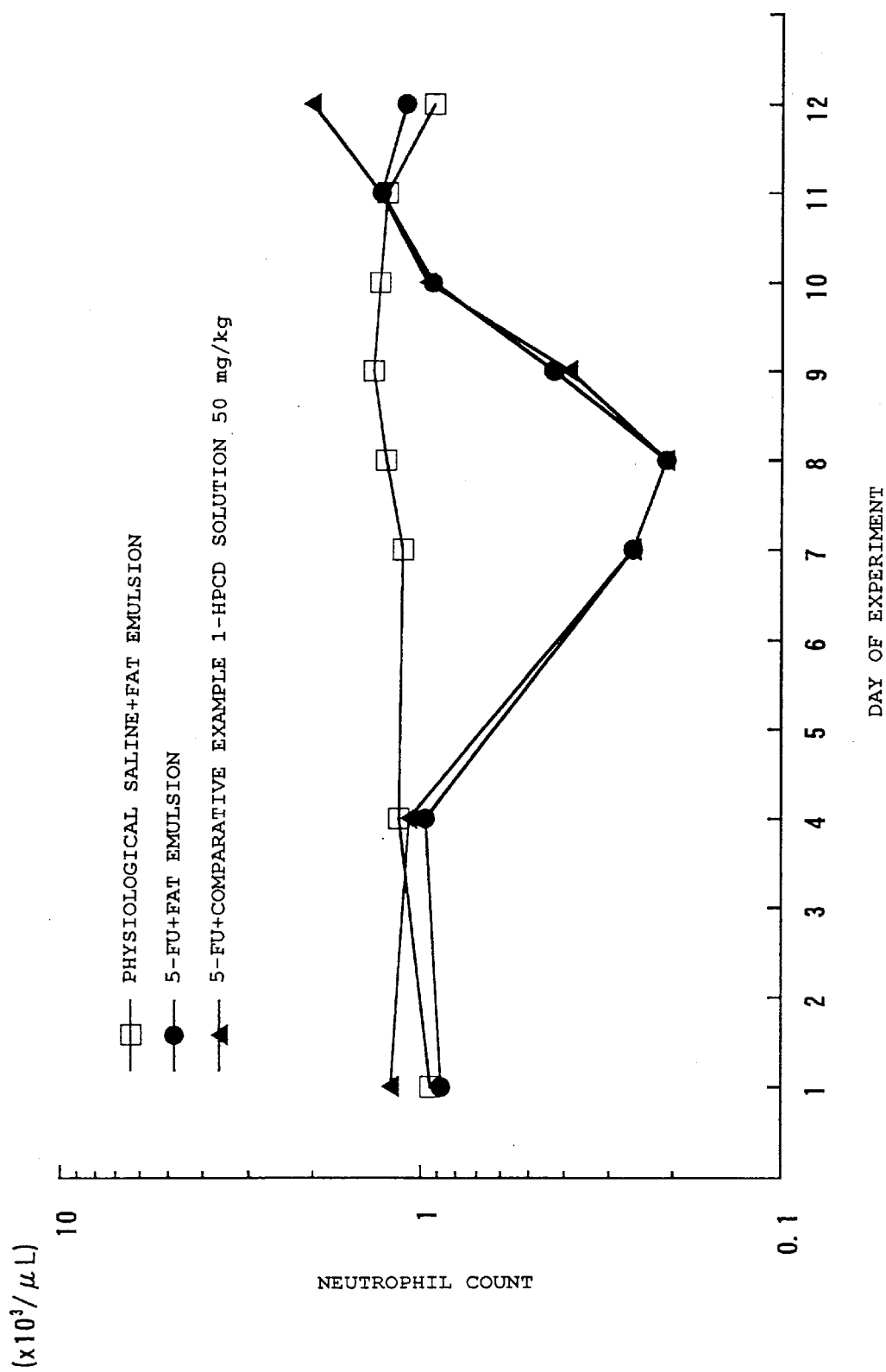

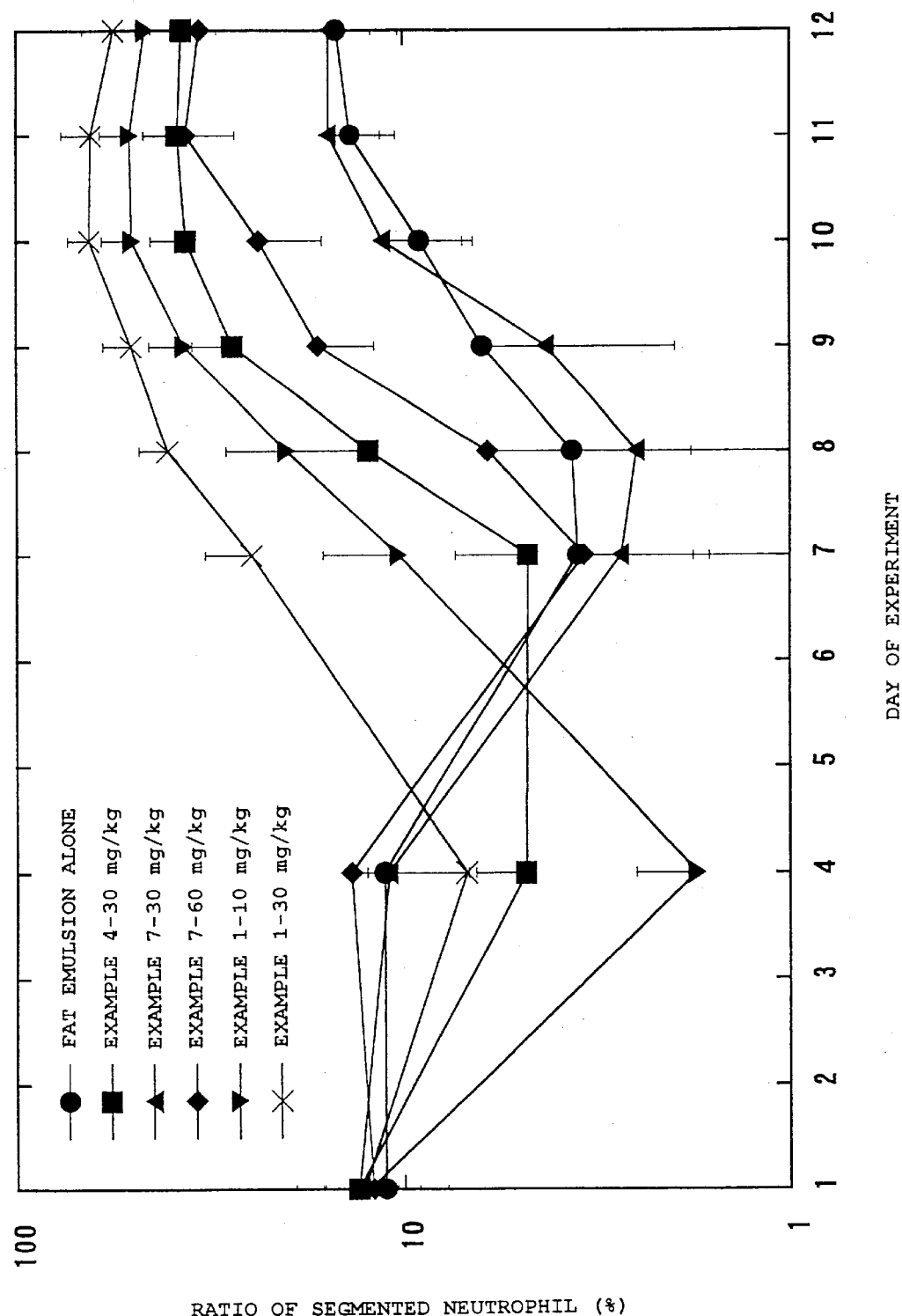

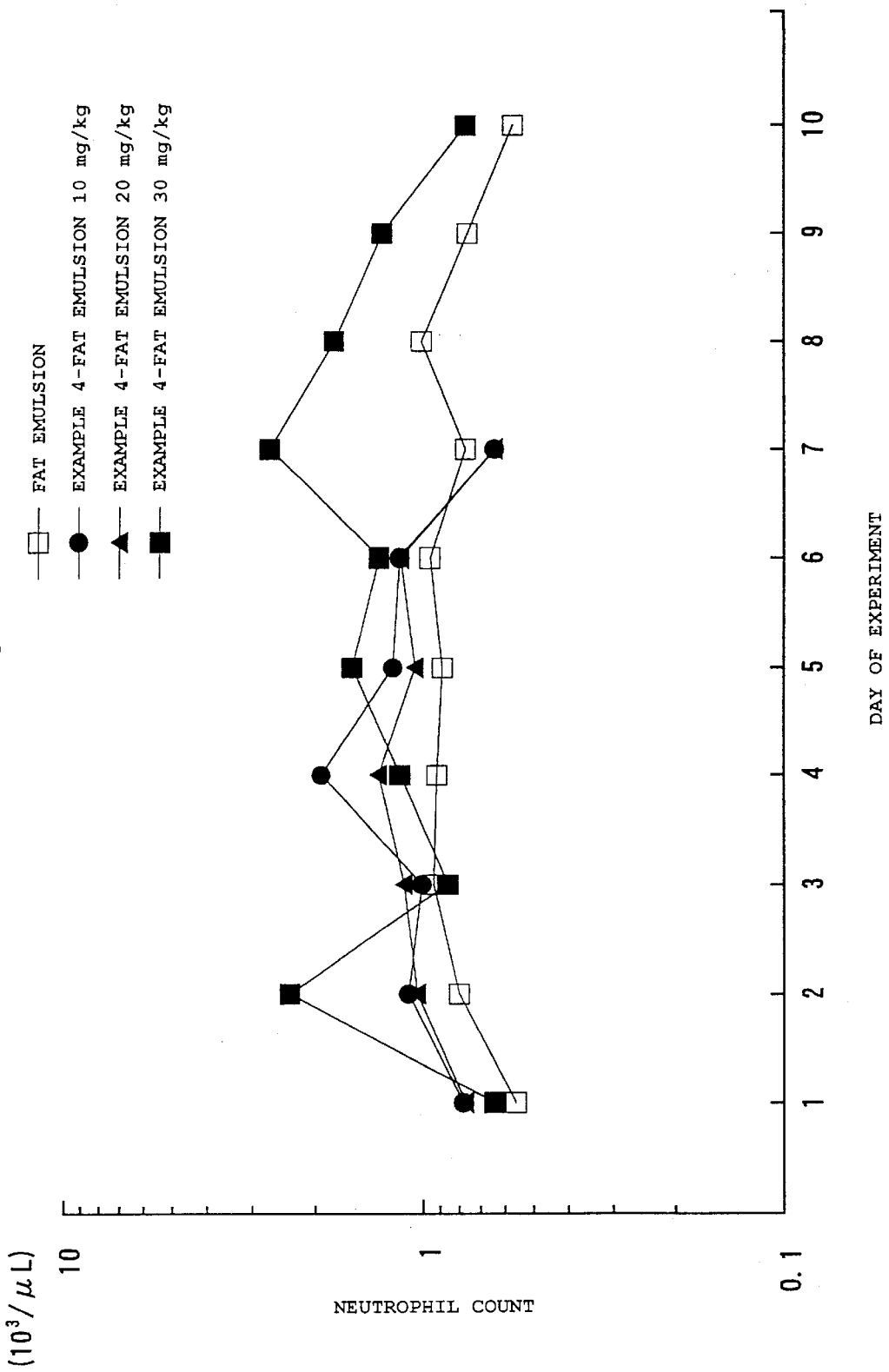

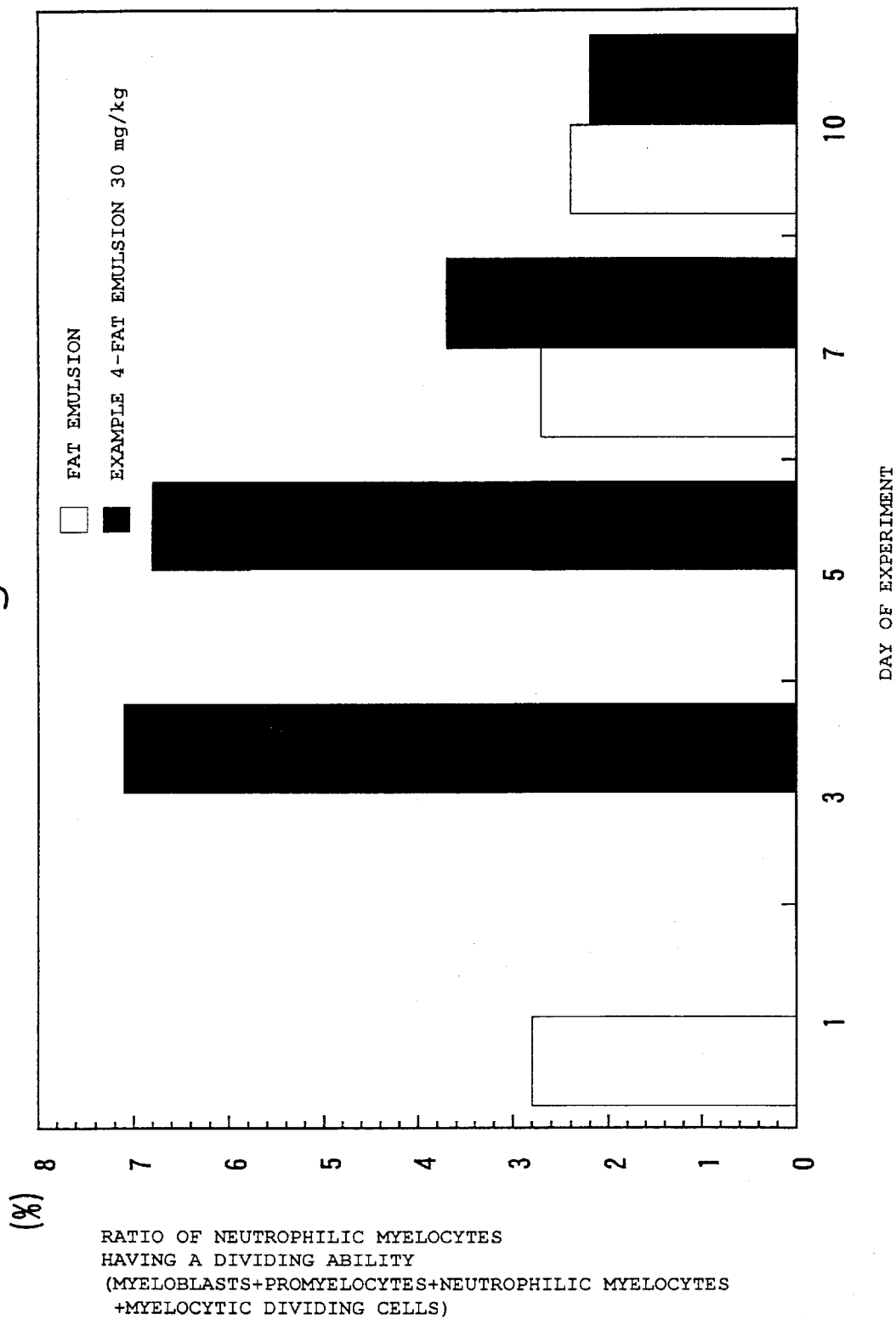

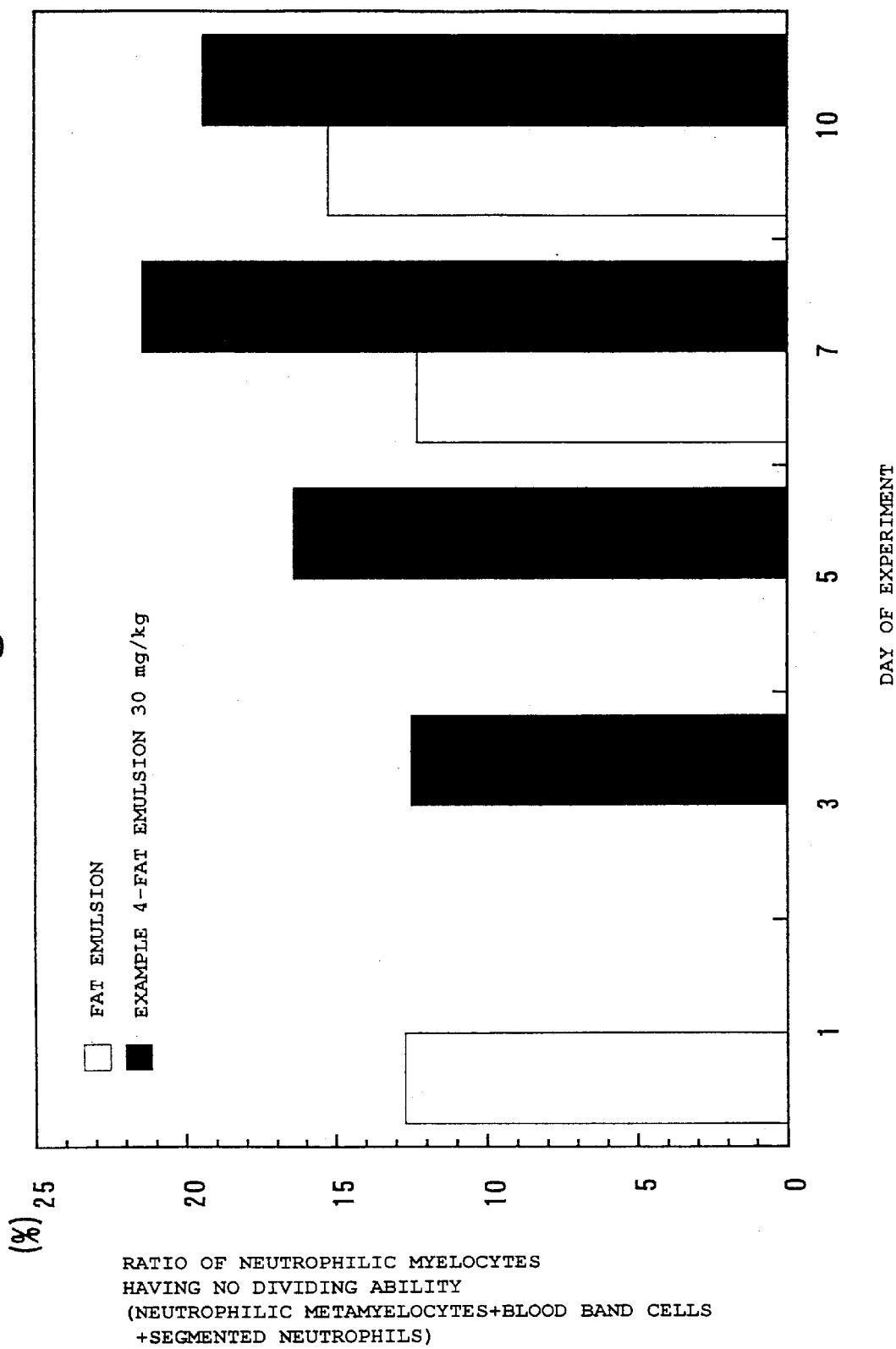

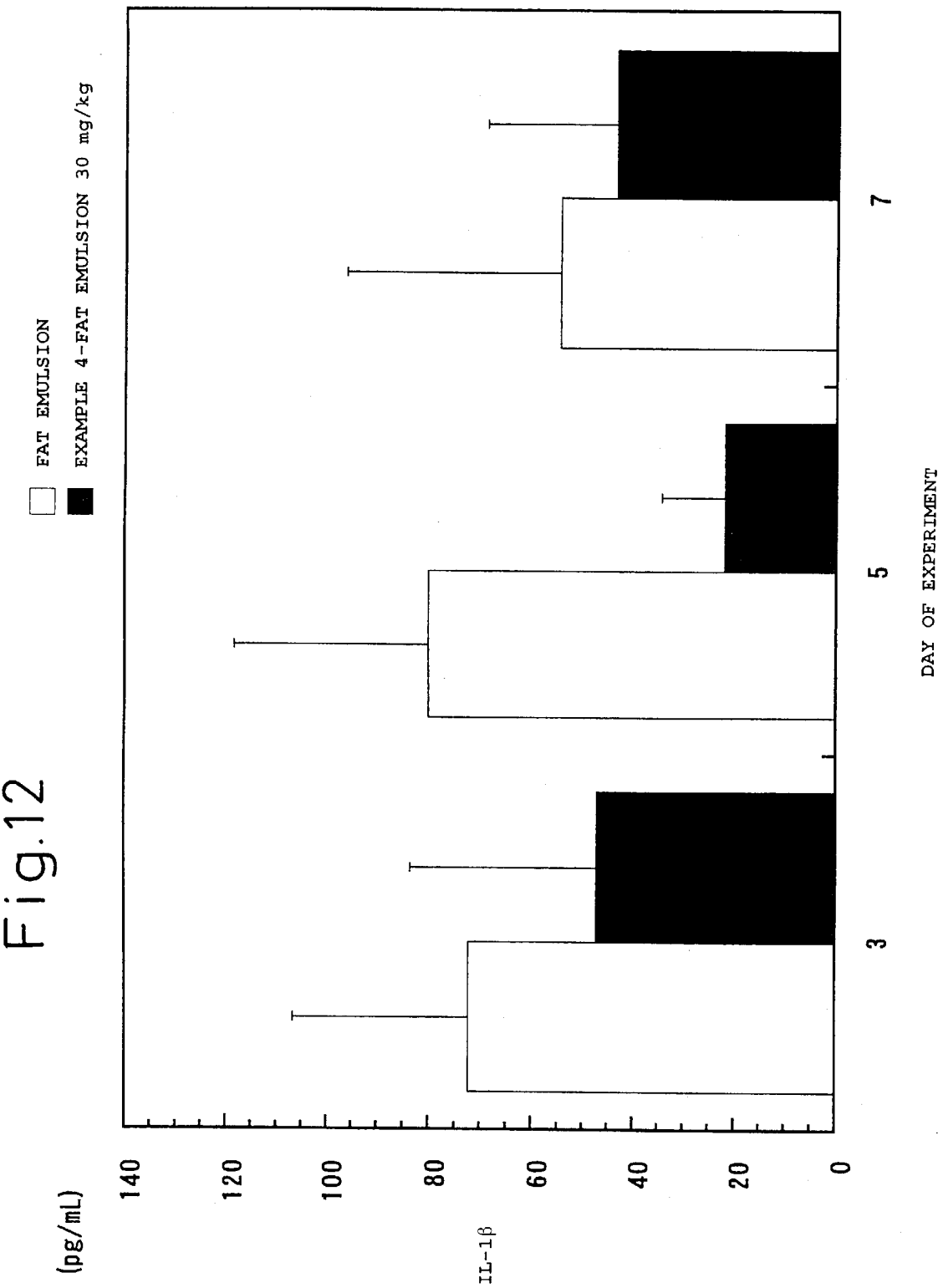

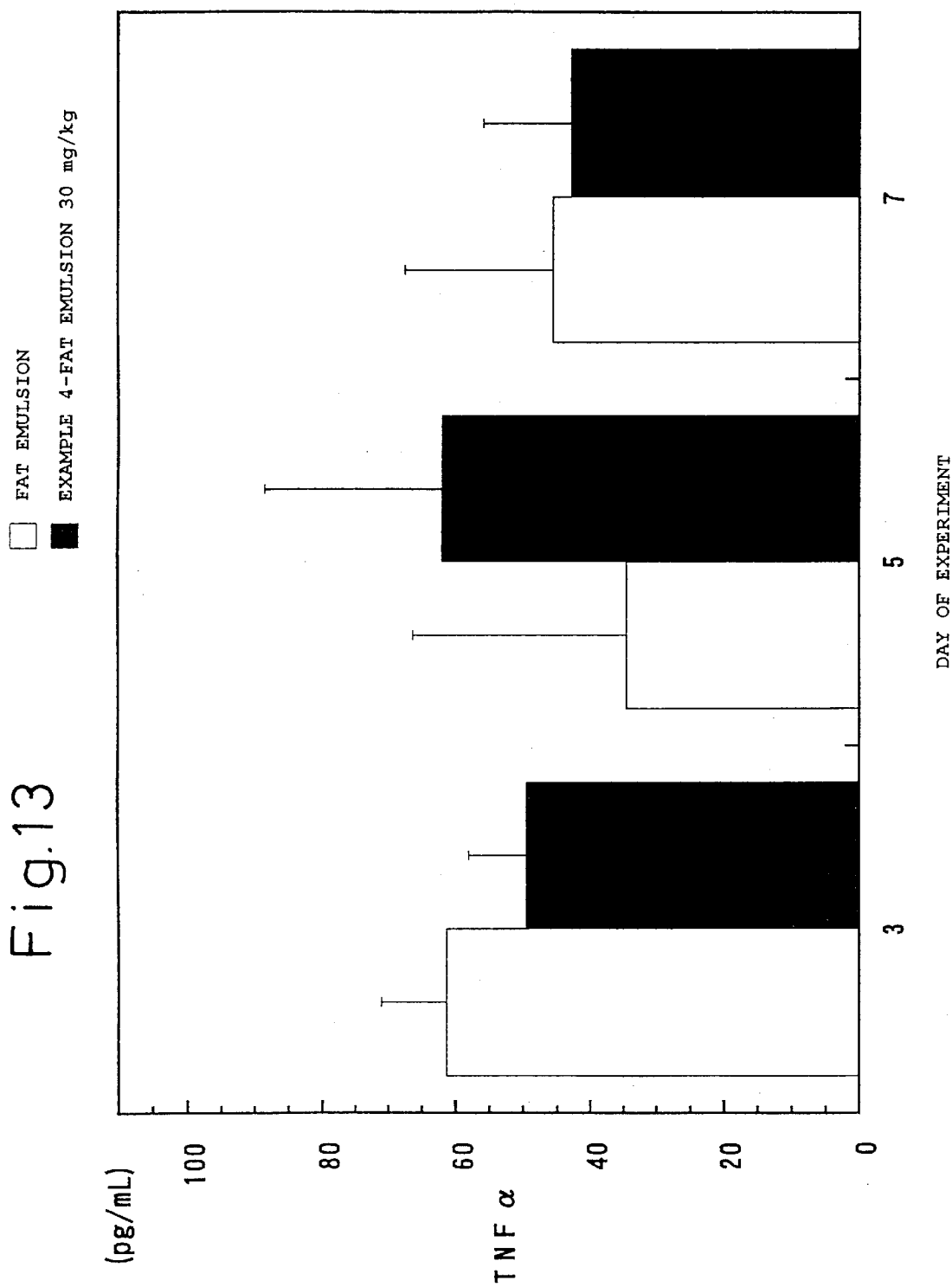

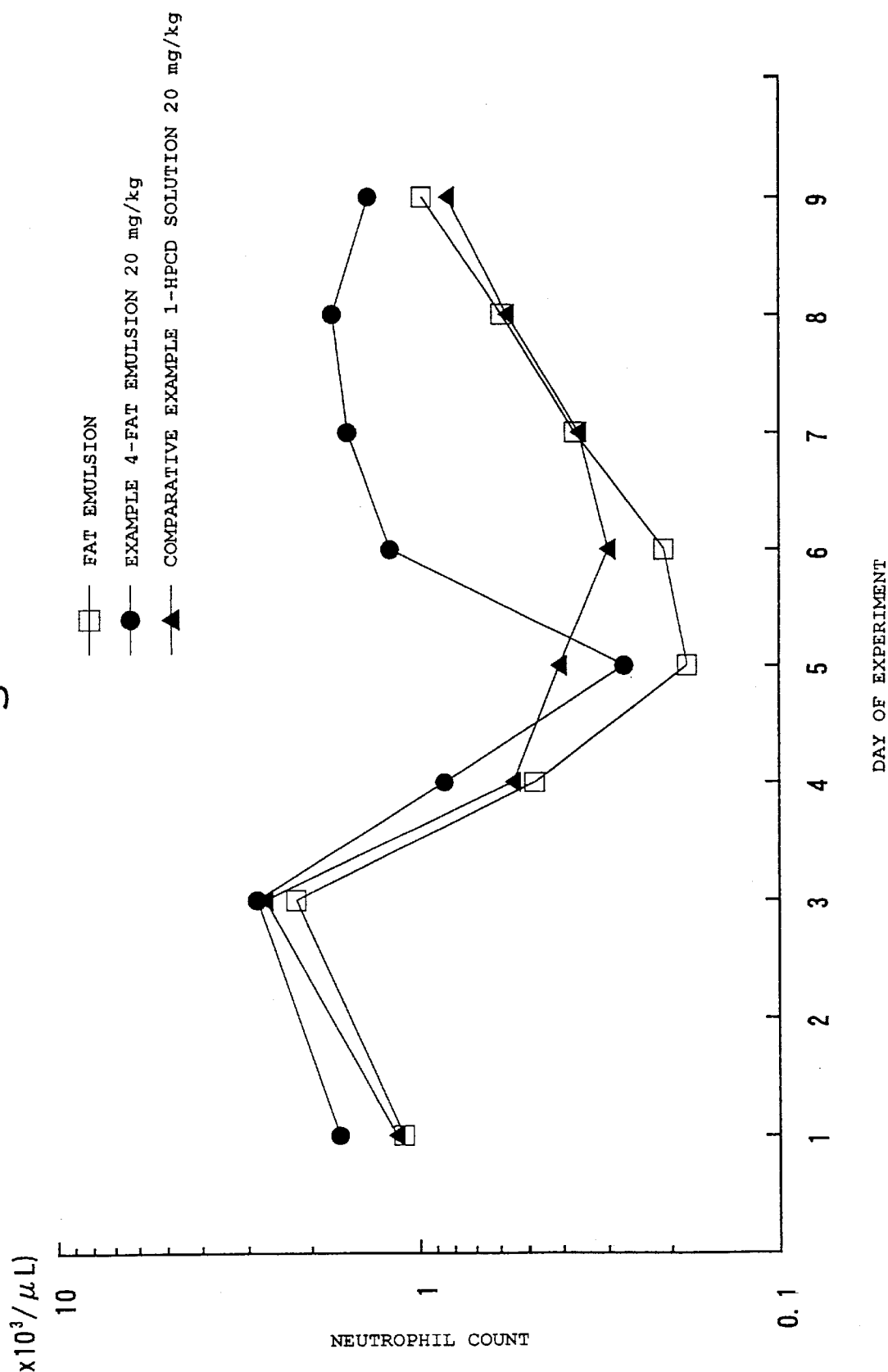

GLUTATHIONE DERIVATIVES AND THEIR DOSAGE FORMS

This application is a 371 of PCT/JP99/02044, filed Apr. 16, 1999, which claims priority to JP 10-106359, filed Apr. 16, 1998.

TECHNICAL FIELD

The present invention relates to glutathione derivatives and their dosage forms that permit an efficient expression of a hematopoiesis promoting activity in the target site of action of the bone marrow when they are administered in the living body for the purpose of promoting hematopoiesis. More specifically, it relates to methods of facilitating the stability in vivo, without affecting the biological activity, of γ-glutamyl S (benzyl) cysteinyl-R(−)-phenyl-glycine by providing the same with a long-chain alkyl or an alkenyl ester having 12 carbons or more, as well as of imparting a structure that is capable of being efficiently distributed in the target organ of bone marrow, and to methods of providing safe and effective dosage forms of colloidal compositions for injections that are an important dosage regimen.

BACKGROUND ART

The administration of chemotherapeutic agents in the treatment of cancer or the suppression of hematopoietic functions by radiotherapy can cause neutropenia and thrombocytopenia as side effects. In neutropenia among them, an immunological activity is decreased as compared to the normal healthy state so that there is an increased risk of being exposed to severe infections. Therefore, granulocyte colony-stimulating factor (G-CSF), a biologically active protein having an effect of promoting the recovery of neutrophil counts in the peripheral blood, has been clinically administered with satisfactory pharmacological results. However, since it has been produced in cultured cells using the gene recombinant technology, its high production cost is posing a problem from a medical economic viewpoint. In addition, the dosage regimen thereof has been established only for injections. Considering-the pains inflicted to patients and the simplicity of use, there is a need for the development-of drugs that can be administered by other dosage forms such as oral drugs in addition to injections.

Under the circumstances in which there is a need for low molecular weight hematopoiesis-promoting substances that can replace biologically active proteinaceous drugs such as G-CSF, that can be presented at low cost, and that can be administered via non-injection routes, γ-glutamyl ethyl ester S (benzyl) cysteinyl-R(−)-phenyl-glycyl ethyl ester (TER199) and its related compounds disclosed in the specification of WO9640205 were found to have an effect of promoting the in vitro colony formation of granulocytes and macrophage precursor cells. It was also confirmed that the compounds have an in vivo effect of promoting recovery of the number of cells such as neutrophils and platelets in the peripheral blood, using rat models in which the hematopoietic functions were suppressed by the administration of a chemotherapeutic agent (5-fluorouracil), although in an experiment where the dosage was as high as 60 to 120 mg/kg body weight and the method of administration (intraperitoneal administration) is not always clinically tolerated. Experiments carried out by the present inventors, however, have revealed that TER199 is very unstable in biological sample solutions such as rat blood and, hence, it is inefficient in exhibiting a hematopoiesis promoting activity. Furthermore, it was found that when high dosages such as were used in Examples of the specification of WO9640205 were administered intravenously for example, it can cause inflammation at the site of administration due to its physical properties such as low solubility and low tissue transfer. The foregoing suggested that TER199 disclosed in the specification of WO9640205 does not have the usefulness of being put into practical use based on the data.

Next, the WO9640205 specification describes that TER199 is an inhibitor of glutathione S-transferase (GST) having glutathione as the basic backbone structure. GST has been reported to be possibly involved in the resistance against anti-cancer agents and alkylating agents, and besides it is known that the effect of inhibiting the activity of GST can be found in, in addition to TER199, ethacrynic acid that is used as a diuretic, indomethacin, ketoprofen etc. that are used as non-steroidal anti-inflammatory drugs (Rinsho Kensa (Laboratory Tests), Vol. 39 (4), pp. 450–453 (1995)).

It is also very likely that the hematopoiesis-promoting activity in the bone marrow is related to the ability to inhibit GST. In fact, it has been reported that ethacrynic acid that has a structure entirely different from that of TER199 has an activity of inducing in vitro the differentiation of leukemia cells in cooperation with activated $D_3$ (Leukemia Research, Vol. 20 (9), pp. 781–789 (1996)).

DISCLOSURE OF THE INVENTION

After intensive research to resolve the above problems associated with the conventional technology, the inventors of the present invention have found the following facts and have completed,the present invention.

Thus, the inventors were able to improve the stability in vivo of γ-glutamyl S (benzyl) cysteinyl-R(−)-phenyl-glycine (TER117) by providing the same with a long-chain alkyl or an alkenyl ester having 12 carbons or more, without affecting the biological activity related to the promotion of hematopoiesis, and to impart a structure that is capable of being efficiently. distributed in the target organ of bone marrow. In this case, consistent results were obtained by any of the following: a monoester in which either one of the carboxyl groups at the two sites in TER177 has been esterified; a diester in which one has been changed to a short- or middle-chain alkyl or alkenyl ester of 12 carbons or less and the other has been changed to a long-chain alkyl or alkenyl ester of 12 carbons or more; or a diester in which both have been changed to long-chain alkyl or alkenyl esters of 12 carbons or more. As used herein, chains having 1 to 2 carbons are defined as the short chains, chains having 3 to 11 carbons as the middle chains, and chains having 12 carbons or more as the long chains. By changing to long-chain esters, stability in vivo, more specifically stability against decomposition by esterase, was enhanced as compared to a diethyl ester TER199 disclosed as a preferred embodiment in WO9640205 specification. On the other hand, it was found in an in vitro experiment that the biological activity related to the promotion of hematopoiesis was equal to that of TER199. Furthermore, in long-chain esters having 12 carbons or more of TER117, the pharmacokinetic parameters, distribution volume and clearance, could be both decreased by using colloidal pharmaceutical compositions such as a fat emulsion, with a resultant discovery that the pharmacological effects can be efficiently exhibited in the target organ of bone marrow and the problem of safety related to the physical properties and physiological effects per se can be avoided.

Thus, the present invention relates to a glutathione derivative represented by the following formula (I):

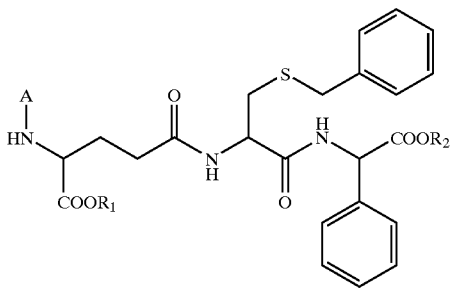

wherein, A represents H or a C1–C20 acyl group; $R_1$ represents a C1–C26 alkyl group or a C3–C26 alkenyl group; and $R_2$ represents H, a C1–C26 alkyl group or a C3–C26 alkenyl group, provided that the case wherein $R_1$ represents a C1–C10 alkyl group or a C3–C10 alkenyl group and $R_2$ represents H, a C1–C10 alkyl group or a C3–C10 alkenyl group is excluded, and a salt thereof.

BRIEF EXPLANATION OF DRAWINGS

FIG. 3 is an experiment on rat plasma described in Example 19. In Comparative Example 1, plasma diluted 400-fold with a BSA solution was used.

FIG. 4 is an experiment on human plasma described in Example 19.

FIG. 5 is a comparison of changes with time in glutathione derivative concentrations in the plasma after intravenous administration in the rabbits.

FIG. 6 is a comparison of pharmacological effects of the glutathione derivatives of Example 4 and Comparative Example 1 in rat models in which the hematopoietic function was suppressed by the administration of 5-fluorouracil (5-FU), and shows changes in neutrophil counts caused by the glutathione derivative of Example 4. Each data is a mean of n=5 to 8.

FIG. 7 is a comparison of pharmacological effects of the glutathione derivatives of Example 4 and Comparative Example 1 in,rat models in which the hematopoietic function was suppressed by the administration of 5-fluorouracil (5-FU), and shows changes in neutrophil counts caused by the glutathione derivative of Comparative Example 1. Each data is a mean of n=6 to 8.

FIG. 8 is a comparison of pharmacological effects of the glutathione derivatives of Examples 1, 4, and 7 in rat models in which the hematopoietic function was suppressed by the administration of 5-fluorouracil (5-FU), and shows changes in the ratio of segmented neutrophils in said rat models. Each data is a mean+/−standard deviation of n=4 to 8.

FIG. 9 shows changes in neutrophil counts in the peripheral blood when the glutathione derivative of Examples 4 was repeatedly administered to normal healthy rats. Each data is a mean of n=6 to 12.

FIG. 10 shows changes in neutrophilic myelocytes (myeloblasts, promyelocytes, neutrophilic myelocytes, myelocytic dividing cells) having a cell division ability when the glutathione derivative of Example 4 was administered to normal healthy rats. Each data is a mean of n=6.

FIG. 11 shows changes in neutrophilic myelocytes (neutrophilic metamyelocytes, blood band cell, segmented neutrophils) having no cell division ability when the glutathione derivative of Example 4 was administered to normal healthy rats. Each data is a mean of n=6 to 12.

FIG. 12 shows changes in the amount of Il-1β in the plasma when the glutathione derivative of Example 4 was administered to normal healthy rats. Each data is a mean+/−standard deviation of n=2 to 3.

FIG. 13 shows changes in the amount of TFNα in the plasma when the glutathione derivative of Example 4 was administered to normal healthy rats. Each data is a mean +/−standard deviation of n=2 to 3.

FIG. 14 is a comparison of pharmacological effects in rabbit models in which the hematopoietic function was suppressed by the administration of cyclophosphamide. Each data is a mean of n=4.

EMBODIMENT FOR CARRYING OUT THE INVENTION

Figure 1:
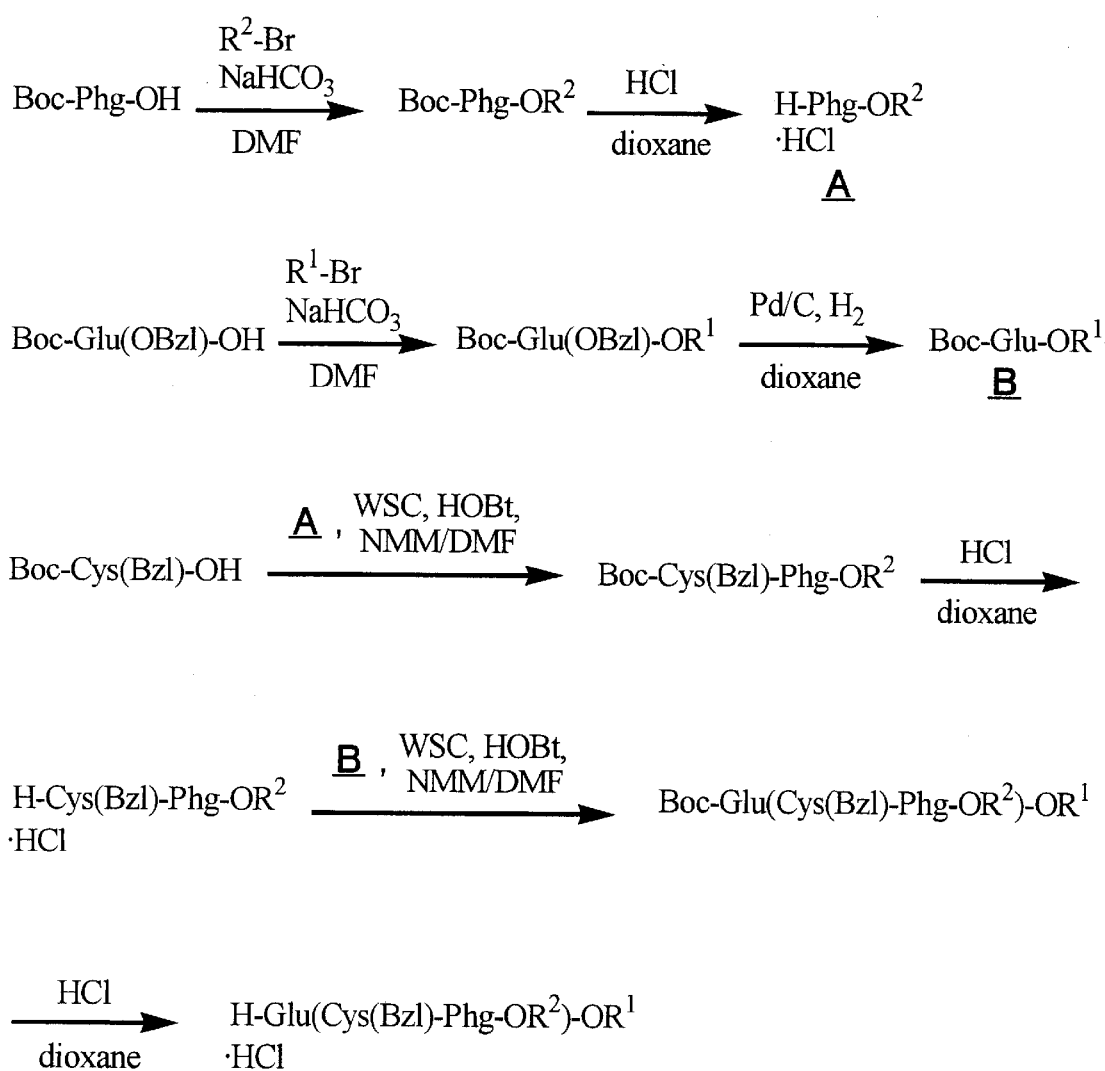
FIG. 1 is a synthetic scheme of a glutathione derivative (medium to long chain alkyl ester) of the present invention.

The glutathione derivative of the present invention can be represented by the following formula (I):

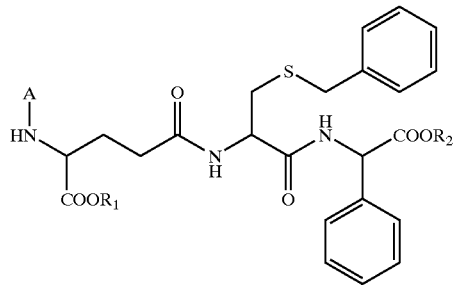

wherein, A represents H or a C1–C20 acyl group; $R_1$ represents a C1–C26 alkyl group or a C3–C26 alkenyl group, and $R_2$ represents H, a C1–C26 alkyl group or a C3–C26 alkenyl group, provided that the case in which $R_1$ represents a C1–C10 alkyl group or a C3–C10 alkenyl group and $R_2$ represents H, a C1–C10 alkyl group or a C3–C10 alkenyl group are excluded.

In the above formula (I), A represents H or a C1–C20 acyl group. Such a C1–C20 acyl group represents a linear or branched acyl group having 1 to 20 carbons among the saturated or unsaturated acyl groups. Examples of such groups include a formyl group, an acetyl group, a propionyl group, a butyryl group, an isobutyryl group, a valeryl group, an isovaleryl group, a hexanoyl group, a heptanoyl group, an octanoyl group, a nonanoyl group, a decanoyl group, a lauroyl group, a myristoyl group, a palmitoyl group, a stearoyl group, a linoleonyl group, and an arachidonoyl group.

Preferred groups of A include H, a formyl group, an acetyl group and the like.

In the above formula (I), $R_1$ represents a C1–C26 alkyl group or a C3–C26 alkenyl group. The C1–C26 alkyl group of such $R_1$ represents a linear or branched alkyl group having 1 to 26 carbons. When a case is thought of in which a linear alkyl or alkenyl group undergoes an enzymatic degradation to form an alcohol, an alkyl group or an alkenyl group having an even number of carbons may be mainly illustrated, since naturally occurring long-chain fatty acids-etc., except abnormal metabolites, generally have an even number of carbons, but alkyl or alkenyl groups having an odd number of carbons are not necessarily excluded.

Examples of such C1–C26 alkyl groups of $R_1$ include a methyl group, an ethyl group, a n-propyl group, an isopropyl group, a n-butyl group, an isobutyl group, a sec-butyl group, a t-butyl group, a n-pentyl group, an isopentyl group, a 3-pentyl group, a hexyl group, an octyl group, a decyl group, a dodecyl group, a tetradecyl group, a hexadecyl group, an octadecyl group, an icosyl group, a docosyl group, a tetracosyl group, and a hexacosyl group.

When $R_1$ is a C3–C26 alkenyl group, such an alkenyl group represents a linear or branched chain alkenyl group having 3 to 26 carbons, and includes, for example, an allyl group, a butenyl group, a pentenyl group, a hexenyl group, a heptenyl group, an octenyl group, a nonenyl group, a decenyl group, a dodecenyl group, a tetradecenyl group, a hexadecenyl group, an octadecenyl group, an octadecadienyl group, an octadecatrienyl group, an icosatrienyl group, an icosatetraenyl group, an icosapentaenyl group, a docosapentaenyl group, docosahexaenyl group, and a tetracosenyl group.

In the above formula (I), $R_2$ represents a C1–C26 alkyl group or a C3–C26 alkenyl group. The C1–C26 alkyl group and the C3–C26 alkenyl group of such $R_1$ represents the same C1–C26 alkyl group and the same C3–C26 alkenyl group as illustrated for R1, respectively.

The compounds of formula I include all combinations of such A, $R_1$, and $R_2$, but the examples of the most preferred combinations are illustrated in Table 1.

carbons is 16 or 18 than when it is 8 to 12 (The Sigma-Aldrich Library of Chemical Safety Data, Edition I), a combination wherein A is H, $R_1$ is an ethyl group, and $R_2$ is a tetradecyl group, a hexadecyl group, an octadecyl group, an octadecadienyl group, octadecatrienyl group, an icosyl group, an icosatrienyl group, an icosatetraenyl group, an icosapentaenyl group or a docosyl group; or a combination wherein A is H, $R_1$ is a tetradecyl group, a hexadecyl group, an octadecyl group or an icosyl group, and $R_2$ is an ethyl group may be mentioned as the most preferred example.

Each of the three amino acids that constitute the glutathione derivative of the present invention has a chiral center, the configuration of which is LLD or LLL, and preferably LLD.

The compounds represented by the above formula (I) may sometimes form acid addition salts or base addition salts. As the acid addition salts, there can be specifically mentioned an addition salt with: a mineral acid such as hydrochloric acid, hydrobromic acid, sulfuric acid, nitric acid and phosphoric acid; an organic acid such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, and ethanesulfonic acid; an acidic amino acid such as aspartic acid and glutamic acid. As a base addition salt, there

TABLE 1

| A | $R_1$ | $R_2$ | A | $R_1$ | $R_2$ | A | $R_1$ | $R_2$ |
|---|---|---|---|---|---|---|---|---|
| H | Ethyl | C12H25 | H | C12H25 | C12H25 | H | C20H41 | Hexyl |
| H | Ethyl | C14H29 | H | C12H25 | C14H29 | H | C20H41 | Octyl |
| H | Ethyl | C16H33 | H | C14H29 | Ethyl | H | Icosatrienyl | Ethyl |
| H | Ethyl | C18H37 | H | C14H29 | Octyl | H | Icosatetraenyl | Ethyl |
| H | Ethyl | Octadecatrienyl | H | C14H29 | Decyl | H | Icosapentaenyl | Ethyl |
| H | Ethyl | Icosatrienyl | H | C14H29 | C12H25 | H | C22H45 | Ethyl |
| H | Ethyl | Icosatetraenyl | H | C16H33 | H | H | C22H45 | Hexyl |
| H | Ethyl | Icosapentaenyl | H | C16H33 | Ethyl | H | C22H45 | Octyl |
| H | Ethyl | Docosahexaenyl | H | C16H33 | Butyl | H | Docosapentataenyl | Ethyl |
| H | Ethyl | C20H41 | H | C16H33 | Butenyl | H | Docosahexaenyl | Ethyl |
| H | Ethyl | C22H45 | H | C16H33 | Hexyl | H | C12H49 | Ethyl |
| H | Ethyl | C24H49 | H | C16H33 | Octyl | H | C12H49 | Butyl |
| H | Ethyl | C26H53 | H | C16H33 | Octenyl | H | C12H49 | Hexyl |
| H | Butenyl | C16H33 | H | C16H33 | Decyl | H | C12H49 | Octyl |
| H | Hexenyl | C16H33 | H | Hexadecenyl | Ethyl | HCO | Ethyl | C16H33 |
| H | Octyl | C12H25 | H | C18H37 | H | HCO | Octyl | C12H25 |
| H | Octyl | C14H29 | H | C18H37 | Ethyl | HCO | Decyl | C12H25 |
| H | Octyl | C16H33 | H | C18H37 | Butyl | HCO | C16H33 | Ethyl |
| H | Decyl | C11H23 | H | C18H37 | Hexyl | HCO | C16H33 | Hexyl |
| H | Decyl | C12H25 | H | C18H37 | Octyl | HCO | C16H33 | Octyl |
| H | Decyl | C14H29 | H | Octadecenyl | Ethyl | Ac | Ethyl | C16H33 |
| H | Decyl | C16H33 | H | Octadecadienyl | Ethyl | Ac | Octyl | C12H25 |
| H | Decenyl | C16H33 | H | Octadecatrienyl | Ethyl | Ac | Decyl | C12H25 |
| H | C11H23 | Decyl | H | C20H41 | H | Ac | C16H33 | Ethyl |
| H | C11H23 | C12H25 | H | C20H41 | Ethyl | Ac | C16H33 | Hexyl |
| H | C12H25 | Decyl | H | C20H41 | Butyl | Ac | C16H33 | Octyl |

As preferred combinations of A, $R_1$, and $R_2$, there can be mentioned: a combination wherein A is H, $R_1$ is an ethyl group, and $R_2$ is a tetradecyl group, a hexadecyl group, an octadecyl group, an octadecadienyl group, an octadecatrienyl group, an icosyl group, an icosatrienyl group, an icosatetraenyl group, an icosapentaenyl group, or a docosyl group; a combination wherein A is H, $R_1$ is a dodecyl group, and $R_2$ is a decyl group or a dodecyl group; a combination wherein A is H, $R_1$ is a tetradecyl group, a hexadecyl group, an octadecyl group or an icosyl group, and $R_2$ is H or an ethyl group; and the like.

Among them, considering the fact it is known that the toxicity of higher alcohols, side products produced as esterase degradation products, is lower when the number of can be specifically mentioned an addition salt, for example, a salt of a monovalent metal such as lithium, sodium, and potassium; a salt of a divalent or trivalent metal such as magnesium, calcium, zinc, and aluminum; an addition salt with a basic amino acid such as lysine and arginine; a salt of an organic ammonium such as ammonium, methyl ammonium, dimethyl ammonium, trimethyl ammonium, benzyl ammonium and monoethanolammonium. Furthermore, the present invention includes hydrates, various solvates, and crystal polymorphic substances of a compound represented by the above formula (I).

The glutathione derivative of the present invention can be synthesized according to methods of peptide synthesis known in the art. As such known methods, there can be mentioned a method of purification after synthesis by a conventional peptide synthetic method described in "Peputidogosei no Kiso to Jikken (Basic and Experimental Peptide Synthesis)" (Nobuo Izumiya, Tetsuo Kato, Haruhiko Aoyagi, Michinori Waki: Maruzen), "Dai 4 Han Jikken Kagaku Koza 22—Yuukigosei IV San/Aminosan/Peputido (The Fourth Edition, Experimental Chemistry Course 22—Organic Synthesis IV Acids/Amino Acids/Peptides)" (Saburo Aimoto, Shoichi Kusumoto, Kuniaki Tatsuta, Yoshihiro Hayakawa, Keiji Yamamoto, Tateaki Wakamiya: Maruzen), and the like. Furthermore, when a side chain and/or a peptide amino terminal and/or a peptide carboxy terminal of each amino acid residue constituting the glutathione derivative of the present invention or a salt thereof has been chemically modified or protected, peptide synthesis is followed by chemical modification, or peptide synthesis is performed using a chemically modified amino acid, or an appropriate reaction condition is selected for the final deprotection of peptide synthesis, as described in a method conventionally known in the art of peptide synthetic chemistry ("Peputidogosei no Kiso to Jikken (Basic and Experimental Peptide Synthesis)" (Nobuo Izumiya, Tetsuo Kato, Haruhiko Aoyagi, Michinori Waki: Maruzen), "Zoku Iyakuhinno Kaihatsu—Dai 14 Kan—Peputido gosei (Development of Pharmaceuticals, Second series, Vol. 14, Peptide Synthesis)", (edited by Haruaki Yajima: Hirokawa Shoten), "Seikagaku Jikken Koza—1—Tanpakushitsu no Kagaku IV—Kagakushushokuto Peputidogosei (Biochemistry Experimental Course—1—Protein Chemistry IV—Chemical Modification and Peptide Synthesis)" (edited by The Japanese Biochemical Society, Tokyo Kagaku Dojin), "Tanpakushitsu no Kagakushushoku (Chemical Modification of Proteins)", the first and second volumes, (Yasunori Ohno, Yuuichi Kanaoka, Fumio Sakiyama, Hiroshi Maeda)).

A preferred synthetic scheme is illustrated in Examples, which, however, does not limit the method of synthesizing the compound of the present invention.

Pharmaceutical compositions having the glutathione derivative of the present invention as an active ingredient may be used in the form of tablets, pills, capsules, powders, granules, liquids, suspensions, emulsions, creams, ointments, aerosols, syrups, troches, lotions, poultices, suppositories, and the like. Using such a form enables administration to humans or animals via an oral, enteric, mucosal, percutaneous, instillation, transmural, and injection administration, and the like.

In the case of injections which is a preferred dosage route, colloidal compositions can be mentioned as a preferred form.

The colloidal compositions of the present invention can be defined as follows:

According to Yakkagaku Daijiten (Comprehensive Dictionary of Pharmaceutical Sciences) (Second edition; Hirokawa Shoten), "colloids" refer to "A kind of a dispersed state. A state in which microparticles (diameter 1–100 nm) that are not directly visible by an optical microscope are dispersed. It sometimes refers only to the dispersed phase (particles). Dispersing solvents or dispersed phase may take the form of solid, liquid, or gas, and all combinations thereof except the gas-gas combination are possible. They are also called the colloidal dispersion system. They are also called colloid." The colloidal compositions of the present invention further include those dispersed particles having a slightly larger particle size than is defined for the common colloid, in which the dispersed particles cannot readily observed by an optical microscopy and represent compositions in the form of solid-liquid, liquid-liquid, or solid and liquid-liquid dispersion liquid in which 90% or more of the dispersed particles have a diameter in the range of 1 nm–1 $\mu$m. Among them, the suspensions and emulsions described in the Japanese Pharmacopeia (the twelfth revised edition) are included in the range in which their particle distribution is limited, and the fat emulsions and liposomes are included herein, and the above colloidal compositions prepared by adding water at the time of use to a dry solid form are also included.

As the colloidal compositions of the present invention, there can be mentioned fat emulsions, liposomes, solid suspensions and the like. Among them, fat emulsions are most preferred since they can be provided at low cost and can be administered by mixing and preparing just prior to use.

In the case of oral administration or enteric administration, colloidal compositions can be used. Fat emulsions can be mentioned as a preferred colloidal composition in this case. In addition to the common fat emulsions described below, as the fat emulsions used herein, there can be mentioned as more preferred examples those fat emulsions that contain middle-chain fatty acids that can be more rapidly metabolized and absorbed in the gastrointestinal tract and that can efficiently deliver active ingredients on the blood stream by routes that go through chylomicron in the lymphatic liquid and those fat emulsions that contain diglycerides. Pharmaceutical compositions that are administered by oral routes etc. for the purpose of lymphotropy are not limited to colloidal compositions, but they may be in the dosage form of tablets, etc.

The fat emulsions of the present invention comprise about 0.1 to 50 (w/v)% of an oil ingredient in the total ingredients (however, the ratio of the oil ingredients in the total ingredients can become one fifth to one thousandth of this, when the fat emulsion and the active ingredient are administered by mixing just prior to use), 1 to 300 parts (weight ratio) of an emulsifier per 100 parts of the oil ingredient, and an appropriate amount of water. Furthermore, an emulsion adjuvant, a stabilizer, an isotonic agent, an antioxidant, a pH adjusting agent, and the like can be added as needed. Furthermore, the surface of particles (hereinafter referred to as the oil phase emulsion) having the oil ingredient of the fat emulsion as the core can be modified with a sugar, a synthetic polymer such as polyethylene glycol, protein and the like to change its distribution in the body thereby resulting in enhanced effects. The concentration of the glutathione derivative that is an active ingredient contained in the fat emulsion, a preferred dosage form of the present invention, is 0.0001–10 (w/v)% relative to the total ingredients.

As an oil ingredient of the fat emulsion of the present invention, there can be used soybean oil, cotton seed oil, safflower oil, corn oil, sesame oil, hydrogenated oil, camellia oil, olive oil, rapeseed oil, palm oil, eucalyptus oil, peanut oil, wheat germ oil, middle-chain fatty acid triglyceride, diglyceride, setyl alcohol, stearyl alcohol, triacetin, eicosapentaenoic acid, docosahexaenoic acid, and the like, but they are not limiting as long as they can be used for pharmaceutical products. Among them, highly purified soybean oil (purity: 99.9% or more are contained as triglyceride, diglyceride and monoglyceride) is most preferable for the fat emulsions to be used as injections.

As the emulsifier of the fat emulsions of the present invention, there can be used lecithins, hydrogenated lecithins, phospholipids and their derivatives, cholesterol and its derivatives, nonionic surfactants and the like, but they are not limiting as long as they can be used for pharmaceutical products. Lecithins, hydrogenated lecithins, and phospholipids may be of any origin, and for example those derived from plants such as soybean oil, those derived from animals such as egg yolk, and the like can be used. Most of lecithins have unsaturated fatty acids, from which unsaturated binding parts are hydrogenated by catalytic reduction etc. to render them resistant to oxidation thereby producing the hydrogenated lecithins. Highly purified dipalmitoyl phosphatidyl choline etc. can be added to the emulsifier. Furthermore, in order to reduce the adsorption to lipo particles of apoproteins in the blood thereby suppressing their incorporation into the liver and to enhance their retention in the blood, it is possible to mix distearoyl-N-(monomethoxy polyethylene glycol succinyl)-phosphatidyl ethanolamine, a phospholipid modified with polyethylene glycol etc.

As the emulsification adjuvant for the fat emulsions of the present invention, there can be used fatty acids of 6–30 carbons, preferably of 12–24 carbons, but they are not limiting as long as they can be added to pharmaceutical products. Among them, naturally occurring fatty acids are most preferred, specific examples of which include stearic acid, oleic acid, linoleic acid, palmitic acid, linolenic acid, and the like. As the physiologically acceptable salts of fatty acids, there can be mentioned alkali metal salts and alkaline earth metal salts.

As the stabilizer of the fat emulsion of the present invention, cholesterol, phosphatidic acid, albumin, vinyl polymers, and nonionic surfactants are preferred, but they are not limiting as long as they can be added to pharmaceutical products. Among them, polyvinylpyrrolidone etc. as the vinyl polymer, polyalkylene, glycol, polyoxyalkylene copolymer, hydrogenated castor oil polyoxyalkylene derivatives, castor oil polyoxyalkylene derivatives etc. as the nonionic surfactants can be used.

As the isotonic agents for the fat emulsions of the present invention, there can be mentioned glycerin, glucose, and the like, but they are not limiting as long as they can be added to pharmaceutical products.

The antioxidants for the fat emulsions of the present invention are preferably blended when said emulsifier is a phospholipid. As such, any pharmaceutically acceptable products can be used, and preferred examples include vitamin E.

As the pH modifier for the fat emulsions of the present invention, sodium hydroxide, hydrochloric acid, etc. can be used, but they are not limiting as long as they are pH modifiers that can be added to pharmaceutical products.

The average size of the oil phase emulsion particles of the fat emulsion of the present invention is preferably about 200–400 nm, but those having a smaller particle diameter of about 5–100 nm can also be mentioned as a preferred example.

As the lipid ingredients constituting the lipid bilayer of the liposome of the present invention, lecithins, hydrogenated lecithins, phospholipids and derivatives thereof, cholesterol and derivatives thereof and the like can be used, but they are not limiting as long as they can be used for pharmaceutical products. Lecithins, hydrogenated lecithins, and phospholipids may be of any origin, and for example those derived from plants such as soybean oil, those derived from animals such as egg yolk, and the like can be used. Most of lecithins have unsaturated fatty acids, from which the unsaturated binding parts are hydrogenated by catalytic reduction etc. to render them resistant to oxidation thereby producing the hydrogenated lecithins. Highly purified phospholipids such as dipalmitoyl phosphatidyl choline etc. can be added as the emulsifier. Furthermore, in order to enhance the retention in the blood, it is possible to mix distearoyl-N-(monomethoxy polyethylene glycol succinyl)-phosphatidyl ethanolamine, a phospholipid modified with polyethylene glycol, etc. In order to enhance the tropism for the target organ, it is also possible to bind immunoglobulins etc. that recognize the antigen of the target organ to the membrane lipid ingredients.

As the suspending agents for the solid suspensions of the present invention, there can be used nonionic surfactants, cellulose ethers, starch and its derivatives, pullulan, vinyl polymers, acrylic acid polymers, gum arabic, alginic acid and its derivatives, agar, gelatin, xanthan gum, lecithins, hydrogenated lecithins, phospholipids and the like, but they are not limiting as long as they are the suspending agents that can be added to pharmaceutical products. Among them, as the nonionic surfactants there can be mentioned polyalkylene glycol, polyoxyalkylene copolymers, hydrogenated castor oil polyoxyalkylene derivatives, castor oil polyoxyalkylene derivatives and the like. As the cellulose ethers, there can be mentioned hydroxy propyl cellulose, hydroxypropyl methyl cellulose, hydroxy ethyl cellulose, methyl cellulose, and the like. As the starch derivatives, there can be mentioned hydroxy ethyl starch, etc. and as the alginic acid derivatives, there can be mentioned alginic acid propylene glycol esters.

Furthermore, sucrose fatty acid esters, polysorbate, sorbitan monofatty acid esters, stearic acid polyoxyl, polyalkylene glycol, and the like can be added as the stabilizer to the solid suspensions of the present invention.

The pharmaceutical compositions having as an active ingredient the glutathione derivative of the present invention may also be included or mixed into microspheres prepared using biodegradable absorbable polymers of polylactic acid, polyglycolic acid, and copolymers thereof and the like, and can be administered via the injection, oral, transmural, enteral, or instillation route.

The colloidal compositions having as an active ingredient the glutathione derivative of the present invention can be prepared by, but not limited to, the following methods:

For the fat emulsion, an oil ingredient such as soybean oil is mixed with an emulsifier such as purified yolk lecithin under heating at 40 to 90° C., to which is then added a required amount of water to conduct rough-emulsification using a mixer. This is then pure-emulsified using a high-pressure injection type homogenizer such as a French press, Manton Gaulin etc., ultrasonication, or dispersion equipment to a homogeneous size-controlled emulsion, which is then filtered and then sterilized by the method of high-pressure steam sterilization etc. to produce the emulsion. The glutathione derivative, an active ingredient, may be added directly in the solid form at the stage of mixing the oil ingredient and the emulsifier or the stage of rough-emulsification, or can be added after being mixed with a trace amount of solvent that can be added to pharmaceutical products such as ethanol, polyethylene glycol, benzyl alcohol, etc. Alternatively, after the active ingredient of glutathione derivative was dissolved in a solvent usable for pharmaceutical products and was filter-sterilized, it can be added to the fat emulsion that was separately rough-emulsified, filtered, and autoclave-sterilized, or it can be mixed prior to the administration in a prepared-at-use manner to obtain a pharmaceutical composition.

For the liposome, a lipid-bilayer constituent such as lecithin, phospholipid, cholesterol etc. and the active ingredient of the glutathione derivative are completely dissolved in a solvent such as chloroform, tetrahydrofuran, etc., from which is the solvent is evaporated using a rotary evaporator etc. to make a cast thin film. The film is then dispersed in an isotonic aqueous solution such as water for injection, a salt, a sugar, etc. by the method of ultrasonication etc. followed by a high-pressure injection type degradation treatment or gel filtration so as to obtain a liposome constituting a pharmaceutical composition having a homogeneous particle size. Alternatively, a pharmaceutical composition comprising a liposome can also be obtained by dissolving a lipid bilayer constituent such as lecithin, phospholipid, etc. and the active ingredient of the glutathione derivative in ethanol, diethyl ether, etc., then injecting it under heating into water for injection at a low speed, and removing these organic solvents by ultrafiltration or evaporation.

For the solid suspension, the active ingredient of the glutathione derivative is subjected to dry-mixing grinding in a medium agitation mill together with a cellulose lower alkyl ether such as hydroxypropyl cellulose and a polyoxyalkylene copolymer such as polyoxyethylene [160] polyoxypropylene [30]glycol, which is suspended in water for injection, and then a solid suspension with a mean particle diameter of 1 $\mu$m or less is prepared using a high-pressure injection type atomizer/dispersion equipment such as a nanomizer and a medium agitation wet grinder such as an apex mill. After filtration, this is subjected to sterilization treatment by a method such as high-pressure steam sterilization to obtain a pharmaceutical composition in the colloidal form.

The pharmaceutical composition of the present invention can be used as a hematopoiesis promoting agent in diseases caused by decreased blood cell production or abnormal blood cell functions, or in harvesting hematopoietic stem cells for peripheral blood stem cell transplantation. As diseases caused by decreased blood cell production or abnormal blood cell functions, there can be mentioned the suppression of hematopoietic function associated with bone marrow transplantation or cancer chemotherapy, myelodysplastic syndrome, pernicious anemia, congenital or idiopathic neutropenia or thrombocytopenia, neutropenia that affects the treatment of human immunodeficiency virus (HIV) infections, neutropenia accompanied by an immunosuppressive therapy (kidney transplantation, liver transplantation etc.), neutropenia that affects the treatment of intractable infections or infantile severe infections, and the like. The pharmaceutical composition of the present invention can also be used for preventive purposes.

The colloidal composition of the present invention can be administered by subcutaneous injection, muscular injection, rapid intravenous injection, or drip infusion singly or after being mixed with an infusion for supply of nutrients comprising sugars, amino acids, electrolytes etc., can be orally or enterally administered. In these cases, the amount given is 0.2 $\mu$g/kg/day–60 mg/kg/day and usually about 20 $\mu$g/kg/day–30 mg/kg/day.

The method of alkyl or alkenyl esterification of a pharmaceutical agent such as γ-glutamyl S (benzyl) cysteinyl-R (−)-phenyl-glycine (TER117) having the activity of inhibiting or binding glutathione S-transferase (GST) to a long chain alkyl or alkenyl having 12 carbons or more when they have carboxy groups, and the method of efficiently developing hematopoiesis-promoting activity in the target organ of bone marrow, or the method of enhancing safety by suppressing the development of non-selective physiological effects related to a variety of functions of GST, said methods being found in the present invention, are not limited to a glutathione derivative such as TER117 but can also be used for glutathione S-transferase-inhibiting or binding pharmaceutical substances such as ethacrynic acid having a completely different structure.

EXAMPLES

The present invention will now be explained in more details with reference to the following examples. However, these examples should not be construed to limit the scope of the present invention.

The abbreviations of the derivatives and the functional groups present in those structures, reagents etc. used in the present invention including the Examples are those commonly used in the field of organic chemistry, and the meanings of them are shown below:

$Et_2O$: diethyl ether, DMF: N,N-dimethylformamide, AcOEt: ethyl acetate, EtOH: ethanol, DMSO: dimethyl sulfoxide, Glu: glutamic acid, Cys: cysteine, Phg: phenylglycine, WSC: 1-(3-dimethylaminopropyl)-3-ethyl carbodiimide hydrochloride, HOBt: 1-hydroxy benzotriazole, NMM: N-methyl morpholine, $SOCl_2$: thionyl chloride, $NaHCO_3$: sodium bicarbonate, Pd/C: palladium on carbon, Boc: t-butoxy carbonyl, Ph: phenyl, Bzl: benzyl, Ac: acetyl.

The glutathione derivatives of the present invention were synthesized by a general route shown in FIG. 1. The specific synthetic examples are shown below.

Preparation Example 1

Synthesis of D-Phg-OEt Hydrochloride $SOCl_2$ (4.3 ml) was added to an EtOH suspension (150 ml) of D-phenylglycine (8.00 g) at −50° C. The cooling of the reaction was stopped and then stirred for 71 hours at room temperature. After concentrating the reaction mixture under reduced pressure, $Et_2O$ was added to the crude crystals and then filtered to obtain the D-Phg-OEt hydrochloride.

Yield: 11.3 g 1H NMR (δ ppm, $CDCl_3$): 1.15 (t, J=7.1 Hz, 3H), 4.08–4.21 (m, 2H) 5.12 (s, 1H) 7.30–7.39 (m, 3H) 7.49–7.59 (m, 2H).

Preparation Example 2

Synthesis of Boc-Cys(Bzl)-D-Phg-OEt

HOBt (1.90 g) was added to a DMF solution (50 ml) of Boc-Cys(Bzl)-OH (4.34 g) and D-Phg-OEt hydrochloride (3.00 g), to which were added N-methylmorpholine (1.65 ml) and WSC (4.00 g) at 0° C. The reaction mixture was stirred at 0° C. for 20 minutes and was further stirred at room temperature for 80 minutes, to which water was added, and extracted with AcOEt. The organic phase was washed with saturated saline, dried with magnesium sulfate anhydride, and then filtered and concentrated. The residue was purified by silica gel chromatography (h-hexane/AcOEt=4/1→2/1) to obtain Boc-Cys(Bzl)-D-Phg-OEt.

Yield: 6.41 g; 1H NMR (δ ppm, $CDCl_3$): 1.21 (t, J=7.1 Hz, 3H) 1.45 (s, 9H) 2.71 (dd, J=8.8 Hz, 4.1 Hz, 1H) 2.86 (dd, J=8.8, 3.7 Hz, 1H) 3.70 (s, 2H) 4.07–4.36 (m, 3H) 5.18–5.38 (m, 1H) 5.51 (d, J=4.4 Hz, 1H) 7.18–7.39 (m, 11H).

Preparation Example 3

Synthesis of Boc-Cys(Bzl)-D-Phg-O(Hexadecyl)

This was obtained by a method similar to that of Preparation Example 2.

1H NMR (δ ppm, $CDCl_3$): 0.88 (t, J=4.4 Hz, 3H) 1.13–1.35 (m, 26H) 1.39–1.61 (m, 11H) 2.71 (dd, J=8.7 Hz, 4.1 Hz, 1H) 2.86 (dd, J=8.7, 3.7 Hz, 1H) 3.70 (s, 2H) 4.11 (t, J=4.1 Hz, 2H) 4.23–4.34 (m, 1H) 5.21–5.34 (m, 1H) 5.51 (d, J=4.6 Hz, 1H) 7.19–7.37 (m, 11H).

Preparation Example 4

Synthesis of Boc-Cys(Bzl)-D-Phg-O(Tetradecyl)

This was obtained by a method similar-to that of Preparation Example 2.

1H NMR (δ ppm, CDCl$_3$): 0.88 (t, J=4.4 Hz, 3H) 1.13–1.35 (m, 22H) 1.39–1.63 (m, 11H) 2.71 (dd, J=8.9 Hz, 4.1 Hz, 1H) 2.86 (dd, J=8.9, 3.7 Hz, 1H) 3.70 (s, 2H) 4.11 (t, J=4.1 Hz, 2H) 4.23–4.35 (m, 1H) 5.21–5.35 (m, 1H) 5.51 (d, J=4.4 Hz, 1H) 7.19–7.39 (m, 11H).

Preparation Example 5

Synthesis of Boc-Cys(Bzl)-D-Phq-O(Dodecyl)

This was obtained by a method similar to that of Preparation Example 2.

1H NMR (δ ppm, CDCl$_3$): 0.88 (t, J=4.4 Hz, 3H) 1.11–1.35 (m, 18H) 1.39–1.66 (m, 11H) 2.71 (dd, J=8.8 Hz, 4.0 Hz, 1H) 2.86 (dd, J=8.8, 3.7 Hz, 1H) 3.70 (s, 2H) 4.11 (t, J=4.1 Hz, 2H) 4.24–4.35 (m, 1H) 5.21–5.35 (m, 1H) 5.51 (d, J=4.4 Hz, 1H) 7.19–7.42 (m, 11H).

Preparation Example 6

Synthesis of Boc-Cys(Bzl)-D-Phg-O(Decyl)

This was obtained by a method similar to that of Preparation Example 2.

1H NMR (δ ppm, CDCl$_3$): 0.88 (t, J=4.4 Hz, 3H) 1.13–1.35 (m, 14H) 1.37–1.66 (m, 11H) 2.71 (dd, J=8.9 Hz, 4.1 Hz, 1H) 2.86 (dd, J=8.9, 3.7 Hz, 1H) 3.70 (s, 2H) 4.11 (t, J=4.1 Hz, 2H) 4.23–4.35 (m, 1H) 5.19–5.35 (m, 1H) 5.51 (d, J=4.4 Hz, 1H) 7.19–7.42 (m, 11H).

Preparation Example 7

Synthesis of Boc-Cys(Bzl)-D-Phg-O(Octyl)

This was obtained by a method similar to that of Preparation Example 2.

1H NMR (δ ppm, CDCl$_3$): 0.87 (t, J=4.4 Hz, 3H) 1.13–1.34 (m, 10H) 1.39–1.66 (m, 11H) 2.71 (dd, J=8.9 Hz, 4.1 Hz, 1H) 2.86 (dd, J=8.9, 3.7 Hz, 1H) 3.70 (s, 2H) 4.12 (t, J=4.2 Hz, 2H) 4.23–4.35 (m, 1H) 5.19–5.35 (m, 1H) 5.51 (d, J=4.4 Hz, 1H) 7.19–7.42 (m, 11H).

Preparation Example 8

Synthesis of Boc-Cys(Bzl)-D-Phg-O(Hexyl)

This was obtained by a method similar to that of Preparation Example 2.

1H NMR (δ ppm, CDCl$_3$): 0.84 (t, J=4.3 Hz, 3H) 1.13–1.30 (m, 6H) 1.37–1.65 (m, 11H) 2.71 (dd, J=8.7 Hz, 4.1 Hz, 1H) 2.86 (dd, J=8.7, 3.7 Hz, 1H) 3.70 (s, 2H) 4.12 (t, J=4.2 Hz, 2H) 4.23–4.39 (m, 1H) 5.19–5.35 (m, 1H) 5.51 (d, J=4.4 Hz, 1H) 7.19–7.42 (m, 11H).

Preparation Example 9

Synthesis of Boc-Glu(OBzl)-O(Octadecyl)

1-Bromooctadecane (4.45 g) and NaHCO$_3$ (1.90 g) were added to a DMF solution (40 ml) of Boc-Glu(OBzl)-OH (1.50 g) and the reaction mixture was stirred at room temperature for 24 hours. Water was added to the reaction mixture, and extracted with AcOEt. The organic phase was washed with water, dried with magnesium sulfate anhydride, and then filtered and concentrated. The residue was purified by silica gel chromatography (n-hexane/AcOEt=25/1→8/1) to obtain Boc-Glu(OBzl)-O(Octadecyl).

Yield: 1.64 g; 1H NMR (δ ppm, CDCl$_3$): 0.88 (t, J=4.4 Hz, 3H) 1.13–1.35 (m, 30H) 1.43 (s, 9H) 1.59–1.66 (m, 2H) 1.90–2.01 (m, 1H) 2.15–2.26 (m, 1H) 2.37–2.55 (m, 2H) 4.11 (t, J=4.3 Hz, 2H) 4.27–4.37 (m, 1H) 5.05–5.16 (m, 1H) 5.12 (s, 2H) 7.29–7.39 (m, 5H).

Preparation Example 10

Synthesis of Boc-Glu(OBzl)-O(Dococyl)

This was obtained by a method similar to that of Preparation Example 9.

1H NMR (δ ppm, CDCl$_3$): 0.88 (t, J=4.4 Hz, 3H) 1.21–1.35 (m, 38H) 1.43 (s, 9H) 1.56–1.66 (m, 2H) 1.89–2.02 (m, 1H) 2.13–2.27 (m, 1H) 2.37–2.53 (m, 2H) 4.11 (t, J=4.1 Hz, 2H) 4.26–4.37 (m, 1H) 5.05–5.15 (m, 1H) 5.12 (s, 2H) 7.29–7.39 (m, 5H).

Preparation Example 11

Synthesis of Boc-Glu(OBzl)-O(Hexadecyl)

This was obtained by a method similar to that of Preparation Example 9.

1H NMR (δ ppm, CDCl$_3$): 0.88 (t, J=4.4 Hz, 3H) 1.21–1.35 (m, 26H) 1.43 (s, 9H) 1.56–1.66 (m, 2H) 1.89–2.02 (m, 1H) 2.13–2.27 (m, 1H) 2.37–2.55 (m, 2H) 4.11 (t, J=4.2 Hz, 2H) 4.27–4.37 (m, 1H) 5.06–5.15 (m, 1H) 5.12 (s, 2H) 7.29–7.39 (m, 5H).

Preparation Example 12

Synthesis of Boc-Glu(OBzl)-O(Tetradecyl)

This was obtained by a method similar to that of Preparation Example 9.

1H NMR (δ ppm, CDCl$_3$): 0.88 (t, J=4.3 Hz, 3H) 1.21–1.37 (m, 22H) 1.44 (s, 9H) 1.58–1.68 (m, 2H) 1.90–2.02 (m, 1H) 2.15–2.26 (m, 1H) 2.37–2.55 (m, 2H) 4.11 (t, J=4.3 Hz, 2H) 4.27–4.37 (m, 1H) 5.06–5.15 (m, 1H) 5.12 (s, 2H) 7.29–7.39 (m, 5H).

Preparation Example 13

Synthesis of Boc-Glu(OBzl)-O(Dodecyl)

This was obtained by a method similar to that of Preparation Example 9.

1H NMR (δ ppm, CDCl$_3$): 0.88 (t, J=4.4 Hz, 3H) 1.21–1.35 (m, 18H) 1.43 (s, 9H) 1.58–1.68 (m, 2H) 1.90–2.02 (m, 1H) 2.13–2.26 (m, 1H) 2.37–2.55 (m, 2H) 4.11 (t, J=4.1 Hz, 2H) 4.27–4.37 (m, 1H) 5.06–5.15 (m, 1H) 5.12 (s, 2H) 7.29–7.39 (m, 5H).

Preparation Example 14

Synthesis of Boc-Glu(OBzl)-O(Decyl)

This was obtained by a method similar to that of Preparation Example 9.

1H NMR (δ ppm, CDCl$_3$): 0.88 (t, J=4.4 Hz, 3H) 1.21–1.35 (m, 14H) 1.43 (s, 9H) 1.58–1.68 (m, 2H)

1.90–2.02 (m, 1H) 2.13–2.26 (m, 1H) 2.37–2.55 (m, 2H) 4.12 (t, J=4.3 Hz, 2H) 4.27–4.37 (m, 1H) 5.06–5.15 (m, 1H) 5.12 (s, 2H) 7.29–7.39 (m, 5H).

Preparation Example 15

Synthesis of Boc-Glu(OBzl)-O(Octyl)

This was obtained by a method similar to that of Preparation Example 9.

1H NMR (δ ppm, CDCl$_3$): 0.88 (t, J=4.4 Hz, 3H) 1.21–1.35 (m, 10H) 1.43 (s, 9H) 1.58–1.68 (m, 2H) 1.90–2.02 (m, 1H) 2.13–2.26 (m, 1H) 2.37–2.55 (m, 2H) 4.12 (t, J=4.3 Hz, 2H) 4.27–4.37 (m, 1H) 5.06–5.15 (m, 1H) 5.12 (s, 2H) 7.29–7.39 (m, 5H).

Preparation Example 16

Synthesis of Boc-Glu(OBzl)-OEt

This was obtained by a method similar to that of Preparation Example 9.

1H NMR (δ ppm, CDCl$_3$): 1.27 (t, J=4.4 Hz, 3H) 1.43 (s, 9H) 1.90–2.02 (m, 1H) 2.15–2.26 (m, 1H) 2.37–2.55 (m, 2H) 4.19 (q, J=4.4 Hz, 2H) 4.27–4.37 (m, 1H) 5.05–5.18 (m, 1H) 5.12 (s, 2H) 7.29–7.39 (m, 5H).

Preparation Example 17

Synthesis of Boc-Glu(Cys(Bzl)-D-Phg-OEt)-O(Octadecyl)

Ten % Pd/C (200 mg) was added to a dioxane solution (40 ml) of Boc-Glu(OBzl)-O(Octadecyl) (1.4.0 g) and the reaction mixture was stirred at an atmosphere of hydrogen gas for 14 hours, and then filtered. The mother liquid was concentrated under reduced pressure. To the residue were added DMF (40 ml), Cys(Bzl)-D-Phg-OEt hydrochloride (945 mg) and HOBt (345 mg) and stirred, to which N-methylmorpholine (0.28 ml) and WSC (670 mg) were added at 0° C. The reaction mixture was stirred at 0° C. for 30 minutes, further stirred at room temperature for 4 hours. Then water was added thereto and extracted with AcOEt. The organic phase was washed with water, dried with magnesium sulfate anhydride, and then filtered and concentrated. The residue was purified by silica gel chromatography (n-hexane/AcOEt=2/1→5/3) to obtain Boc-Glu(Cys(Bzl)-D-Phg-OEt)-O(Octadecyl).

Yield: 1.75 g 1H NMR (δ ppm, CDCl$_3$): 0.88 (t, J=4.3 Hz, 3H) 1.18 (t, J=4.4 Hz, 3H) 1.21–1.36 (m, 30H) 1.44 (s, 9H) 1.54–1.66 (m, 2H) 1.84–1.98 (m, 1H) 2.13–2.33 (m, 3H) 2.69 (dd, J=8.7 Hz, 4.3 Hz, 1H) 2.86 (dd, J=8.7 Hz, 3.8 Hz, 1H) 3.71 (s, 2H) 4.07–4.26 (m, 4H) 4.32–4.42 (m, 1H) 4.48–4.58 (m, 1H) 5.30 (d, J=5.0 Hz, 1H) 5.48 (d, J=4.6 Hz, 1H) 6.67 (d, J=4.6 Hz, 1H) 7.20–7.40 (m, 11H).

Example 1

Synthesis of Glu(Cys(Bzl)-D-Phg-OEt)-O(Octadecyl)hydrochloride

A dioxane solution (5 ml) of 4N hydrochloric acid was added to a dioxane solution (10 ml) of Bog-Glu(Cys(Bzl)-D-Phg-OEt)-O(Octadecyl) (1.73 g). The reaction mixture was stirred at room temperature for 20 hours and concentrated under reduced pressure. The residue was dissolved in dioxane, and Et$_2$O was added thereto and stirred overnight. The solid that deposited was filtered and, after washing with Et$_2$O, dried to obtain Glu(Cys(Bzl)-D-Phg-OEt)-O(Octadecyl)hydrochloride.

Yield: 1.50 g; 1H NMR (δ ppm, CDCl$_3$): 0.88 (t, J=4.4 Hz, 3H) 1.16 (t, J=4.4 Hz, 3H) 1.21–1.34 (m, 30H) 1.56–1.66 (m, 2H) 2.21–2.34 (m, 1H) 2.41–2.52 (m, 1H) 2.62–2.72 (m, 2H) 2.80 (d, J=4.4 Hz, 2H) 3.66 (s, 2H) 4.03–4.25 (m, 5H) 4.56–4.64 (m, 1H) 5.51 (d, J=4.6 Hz, 1H) 7.13–7.34 (m, 10H) 7.74 (d, J=4.6 Hz, 1H) 7.87 (d, J=5.0 Hz, 1H) 8.72 (brs, 3H).

By using methods similar to those described in the above Example and Preparation Examples and organic chemical methods known to a person skilled in the art, the following compounds were prepared.

Example 2

Glu(Cys(Bzl)-D-Phg-OEt)-O(Docosyl)hydrochloride

1H NMR (δ ppm, CDCl$_3$): 0.88 (t, J=4.4 Hz, 3H) 1.16 (t, J=4.4 Hz, 3H) 1.20–1.34 (m, 38H) 1.54–1.66 (m, 2H) 2.20–2.36 (m, 1H) 2.39–2.54 (m, 1H) 2.62–2.74 (m, 2H) 2.80 (d, J=4.1 Hz, 2H) 3.67 (s, 2H) 4.05–4.25 (m, 5H) 4.54–4.66 (m, 1H) 5.51 (d, J=4.4 Hz, 1H) 7.16–7.39 (m, 10H) 7.73 (d, J=4.4 Hz, 1H) 7.87 (d, J=4.7 Hz, 1H) 8.70 (brs, 3H).

Example 3

Glu(Cys(Bzl)-D-Phq-OEt)-O(9,12,15-Octadecatrienyl)hydrochloride

1H NMR (δ ppm, CDCl$_3$): 0.97 (t, J=4.6 Hz, 3H) 1.16 (t, J=4.4 Hz, 3H) 1.23–1.43 (m, 10H) 1.56–1.69 (m, 2H) 1.93–2.13 (m, 4H) 2.20–2.36 (m, 1H) 2.39–2.52 (m, 1H) 2.59–2.89 (m, 8H) 3.65 (s, 2H) 4.03–4.26 (m, 5H) 4.57–4.69 (m, 1H) 5.28–5.64 (m, 6H) 5.50 (d, J=4.4 Hz, 1H) 7.15–7.41 (m, 10H) 7.76 (d, J=4.4 Hz, 1H) 7.87 (d, J=4.9 Hz, 1H) 8.69 (brs, 3H).

Example 4

Glu(Cys(Bzl)-D-Phg-OEt)-O(Hexadecyl)hydrochloride

1H NMR (δ ppm, CDCl$_3$): 0.88 (t, J=4.4 Hz, 3H) 1.16 (t, J=4.4 Hz, 3H) 1.20–1.34 (m, 26H) 1.56–1.66 (m, 2H) 2.21–2.36 (m, 1H) 2.41–2.52 (m, 1H) 2.61–2.72 (m, 2H) 2.79 (d, J=4.4 Hz, 2H) 3.66 (s, 2H) 4.03–4.26 (m, 5H) 4.56–4.64 (m, 1H) 5.50 (d, J=4.5 Hz, 1H) 7.15–7.38 (m, 10H) 7.74 (d, J=4.5 Hz, 1H) 7.87 (d, J=5.0 Hz, 1H) 8.72 (brs, 3H)

Example 5

Ac-Glu(Cys(Bzl)-D-Phg-OEt)-O(Hexadecyl)

1H NMR (δ ppm, CDCl$_3$): 0.88 (t, J=4.4 Hz, 3H) 1.18–1.36 (m, 29H) 1.57–1.69 (m, 2H) 1.92–2.05 (m, 1H). 2.01 (s, 3H) 2.16–2.36 (m, 3H) 2.71 (dd, J=8.9 Hz, 4.4 Hz, 1H) 2.85 (dd, J=8.9 Hz, 4.1 Hz, 1H) 3.71 (s, 2H) 4.07–4.26 (m, 5H) 4.52–4.58 (m, 1H) 4.64–4.70 (m, 1H) 5.49 (d, J=4.4 Hz, 1H) 6.55 (d, J=4.7 Hz, 1H) 6.83 (d, J=4.9 Hz, 1H) 7.20–7.38 (m, 10H) 7.40 (d, J=4.4 Hz, 1H).

Example 6

Glu(Cys(Bzl)-D-Phg-OEt)-O(Tetradecyl)hydrochloride

1H NMR (δ ppm, CDCl$_3$): 0.88 (t, J=4.6 Hz, 3H) 1.16 (t, J=4.4 Hz, 3H) 1.20–1.34 (m, 22H) 1.56–1.66 (m, 2H) 2.21–2.36 (m, 1H) 2.41–2.52 (m, 1H) 2.61–2.72 (m, 2H)

2.80 (d, J=4.4 Hz, 2H) 3.66 (s, 2H) 4.03–4.26 (m, 5H), 4.54–4.64 (m, 1H) 5.50 (d,. J=4.5 Hz, 1H) 7.15–7.38 (m, 10H) 7.73 (d, J=4.5 Hz, 1H) 7.87 (d, J=5.0 Hz, 1H) 8.71 (brs, 3H).

Example 7

Glu(Cys(Bzl)-D-Phg-OEt)-O(Dodecyl) hydrochloride

1H NMR (δ ppm, CDCl$_3$): 0.88 (t, J=4.6 Hz, 3H) 1.16 (t, J=4.4 Hz, 3H) 1.20–1.34 (m, 18H) 1.56–1.66 (m, 2H) 2.20–2.36 (m, 1H) 2.41–2.52 (m, 1H) 2.61–2.72 (m, 2H) 2.79 (d, J=4.3 Hz, 2H) 3.66 (s, 2H) 4.03–4.26 (m, 5H) 4.54–4.64 (m, 1H) 5.50 (d, J=4.4 Hz, 1H) 7.15–7.38 (m, 10H) 7.73 (d, J=4.4 Hz, 1H) 7.86 (d, J=4.9 Hz, 1H) 8.70 (brs, 3H).

Example 8

Glu(Cys(Bzl)-D-Phg-O(Hexadecyl))-OEt Hydrochloride

1H NMR (δ ppm, CDCl$_3$): 0.88 (t, J=4.1 Hz, 3H) 1.07–1.34 (m, 29H) 1.46–1.56 (m, 2H) 2.21–2.36 (m, 1H) 2.41–2.52 (m, 1H) 2.61–2.72 (m, 2H) 2.79 (d, J=4.0 Hz, 2H) 3.67 (s, 2H) 4.00–4.25 (m, 5H) 4.56–4.64 (m, 1H) 5.50 (d, J=4.5 Hz, 1H) 7.16–7.38 (m, 10H) 7.75 (d, J=4.5 Hz, 1H) 7.82 (d, J=4.9 Hz, 1H) 8.73 (brs, 3H).

Example 9

Glu(Cys(Bzl)-D-Phg-O(Tetradecyl))-OEt Hydrochloride

1H NMR (δ ppm, CDCl$_3$): 0.88 (t, J=4.4 Hz, 3H) 1.06–1.34 (m, 25H) 1.46–1.56 (m, 2H) 2.21–2.36 (m, 1H) 2.39–2.52 (m, 1H) 2.59–2.70 (m, 2H) 2.78 (d, J=4.0 Hz, 2H) 3.66 (s, 2H) 4.00–4.25 (m, 5H) 4.56–4.64 (m, 1H) 5.50 (d, J=4.4 Hz, 1H) 7.15–7.39 (m, 10H) 7.75 (d, J=4.4 Hz, 1H) 7.82 (d, J=4.4 Hz, 1H) 8.72 (brs, 3H).

Example 10

Glu(Cys(Bzl)-D-Phg-O(Dodecyl))-OEt Hydrochloride

1H NMR (δ ppm, CDCl$_3$): 0.88 (t, J=4.4 Hz, 3H) 1.07–1.36 (m, 21H) 1.46–1.56 (m, 2H) 2.23–2.36 (m, 1H) 2.39–2.52 (m, 1H) 2.59–2.70 (m, 2H) 2.78 (d, J=4.3 Hz, 2H) 3.66 (s, 2H) 4.00–4.30 (m, 5H) 4.57–4.69 (m, 1H) 5.50 (d, J=4.4 Hz, 1H) 7.16–7.43 (m, 10H) 7.75 (d, J=4.4 Hz, 1H) 7.82 (d, J=4.9 Hz, 1H) 8.73 (brs, 3H).

Example 11

Glu(Cys(Bzl)-D-Phg-O(Hexadecyl))Hydrochloride

1H NMR (δ ppm, CDCl$_3$): 0.85 (t, J=4.2 Hz, 3H) 1.17–1.36 (m, 26H) 1.54–1.66 (m, 2H) 1.95–2.12 (m, 2H) 2.26–2.53 (m, 3H) 2.62 (dd, J=8.5 Hz, 3.7 Hz, 1H) 3.72 (s, 2H) 4.04 (t, J=4.1 Hz, 1H) 4.14 (t, J=4.1 Hz, 2H) 4.75–4.85 (m, 1H) 5.36–5.43 (m, 1H) 7.17–7.46 (m, 10H) 8.29 (d, J=5.4 Hz, 1H) 9.05 (d, J=4.9 Hz, 1H).

Furthermore, by using the intermediates synthesized in the above Preparation Examples, the following compounds were prepared.

Example 12

Glu(Cys(Bzl)-D-Phg-O(Hexyl))-O(tetradecyl) hydrochloride

Example 13

Glu(Cys(Bzl)-D-Phg-O(Hexyl))-O(hexadecyl) hydrochloride

Example 14

Glu(Cys(Bzl)-D-Phg-O(Octyl))-O(dodecyl) hydrochloride

Example 15

Glu(Cys(Bzl)-D-Phg-O(Octyl))-O(tetradecyl) hydrochloride

Example 16

Glu(Cys(Bzl)-D-Phg-O(Decyl))-O(dodecyl) hydrochloride

Similarly, the following comparative compounds were prepared.

Comparative Example 1

Glu(Cys(Bzl)-D-Phg-O(Et))-O(Et)hydrochloride

TER199 mentioned above.

Comparative Example 2

Glu(Cys(Bzl)-D-Phg-O(Octyl))-O(Et)hydrochloride

Comparative Example 3

Glu(Cys(Bzl)-D-Phg-OH)-OH Hydrochloride

TER117 mentioned above.

Comparative Example 4

Glu(Cys(Bzl)-D-Phg-O(Decyl))-OEt Hydrochloride

Specific examples for preparation of the colloidal compositions of the glutathione derivatives of the present invention are shown below.

Example 17

Preparation of the fat emulsion having as an active ingredient the glutathione derivative of Example 4 was carried out using a high-pressure injection type homogenizer.

(1) The high-pressure injection type homogenizer used was Nanomizer LA from Nanomizer K.K. Purified yolk lecithin, purified soybean oil, and glycerin used were those that can be intravenously injected.

(2) Purified yolk lecithin 6 g and purified soybean oil 55 g were mixed by a mixer while heating to homogeneity. To this was added 560 mg of the glutathione derivative of Example 4 and was further stirred to homogeneity. A suitable amount of glycerin and water for injection were added and rough-emulsified by a mixer, and pH was adjusted to 7.4 with an aqueous solution of sodium hydroxide. Water was further added to a total amount of 560 g, which was pure-emulsified using the Nanomizer LA at an emulsification pressure of 550 kgf/cm² by passing it through the emulsion part for 11 times. The pure-emulsified product was filtered through 1.2 μm filter, and then included in an appropriate glass vial.

(3) The pharmaceutical composition of the glutathione derivative thus obtained was found to have an average diameter (standard deviation)=174.4 nm (75.0 nm), 194.5 nm (77.6 nm), and 189.1 nm (87.9 nm) when the particle distribution of the oil phase emulsion particles thereof was determined three times using NICOMP-370 (Nozaki Sangyo) by the dynamic light scattering method. When the emulsion was crushed with tetrahydrofuran before and after filtration with a 1.2 μm filter and the content of the glutathione derivative of Example 4 was measured by HPLC, it was confirmed that the content of 90% or more of that before filtration was retained, homogeneity was good, and the glutathione derivative of Example 4 was stably mixed in the oil phase emulsion particles. When an alcohol solution of the glutathione derivative of Example 4 was mixed with water for injection at a volume ratio of 5% or less so as to obtain the almost same final concentration of 1 mg/ml, the glutathione derivative immediately crystallized and the content after filtration with a 1.2 μm filter was confirmed to become 75% or less.

Example 18

The glutathione derivative obtained in Example 4 was prepared by the method of mixing with the fat emulsion on a small scale.

(1) According to the method of Example 17, an empty fat emulsion that includes no glutathione derivative was prepared. It was included in a glass vial and autoclave-sterilized, which was stored refrigerated so as to be used when needed.

(2) The glutathione derivative of Example 4 dissolved at 40 mg/ml in a 4:1 mixture of ethanol:benzyl alcohol was mixed with the empty fat emulsion obtained in (1) at a volume ratio of 2.5–7.5%.

(3) The pharmaceutical composition thus obtained had a particle distribution of the oil phase emulsion equal to that of the empty fat emulsion of (1) even after the passage of 5 hours after mixing, and the content of the glutathione derivative in the 1.2 μm filter pass fraction retained 90% or more of the feed amount.

The effectiveness of the glutathione derivatives synthesized in Examples 1–16 was confirmed as shown below.

Example 19

Comparison of the Physiological Stability of the Glutathione Derivative (1) Bovine serum albumin (hereinafter referred to as BSA), Dulbecco's phosphate buffered saline (hereinafter referred to as D-PBS), swine liver esterase, and rabbit liver esterase were purchased from Sigma, 6-week old male SD rats were purchased from Nippon SLC, and 12-week old or older male Japanese white rabbits were purchased from Ichikawaya. On the day of the incubation experiment described below, blood was drawn from the animals in the presence of heparin, and plasma was separated therefrom for use. Human plasma was obtained from normal healthy males after obtaining their consent.

(2) The glutathione derivatives described in the Examples and Comparative Examples of the present invention were incubated for a fixed time in an enzyme solution having the following composition. Acetonitrile was added to the reaction mixture to inactivate the enzyme thereby to stop the reaction. The concentration of the glutathione derivatives in the deproteinized supernatant was measured by HPLC. For each time point of the esterase enzyme experiment, the mean values from two measurement or more were determined, and for the rats and rabbits the mean values of plasma samples from three individuals were determined. For some of the experiment data, changes with time of percentages relative to initial concentration of the glutathione derivative are shown in FIGS. 2 to 4.

Swine liver esterase and rabbit liver esterase experiment
   30 mg-BSA/ml-D-PBS (pH 7.4): 36 to 45 parts
   Swine or rabbit liver esterase/D-PBS: 4–5 parts
   10 mg-glutathione derivative/ml-ethanol: one part (the final concentration in the reaction mixture is 196–244 μg/ml)

Rat, rabbit, and human plasma
   Heparinized plasma: 30 to 40 parts
   (rat plasma was diluted, as needed, with 30 mg-BSA/ml-D-PBS (pH 7.4) for use)
   10 mg-glutathione derivative/ml-ethanol: one part (the final concentration in the reaction mixture is 250–323 μg/ml)

Figure 2:
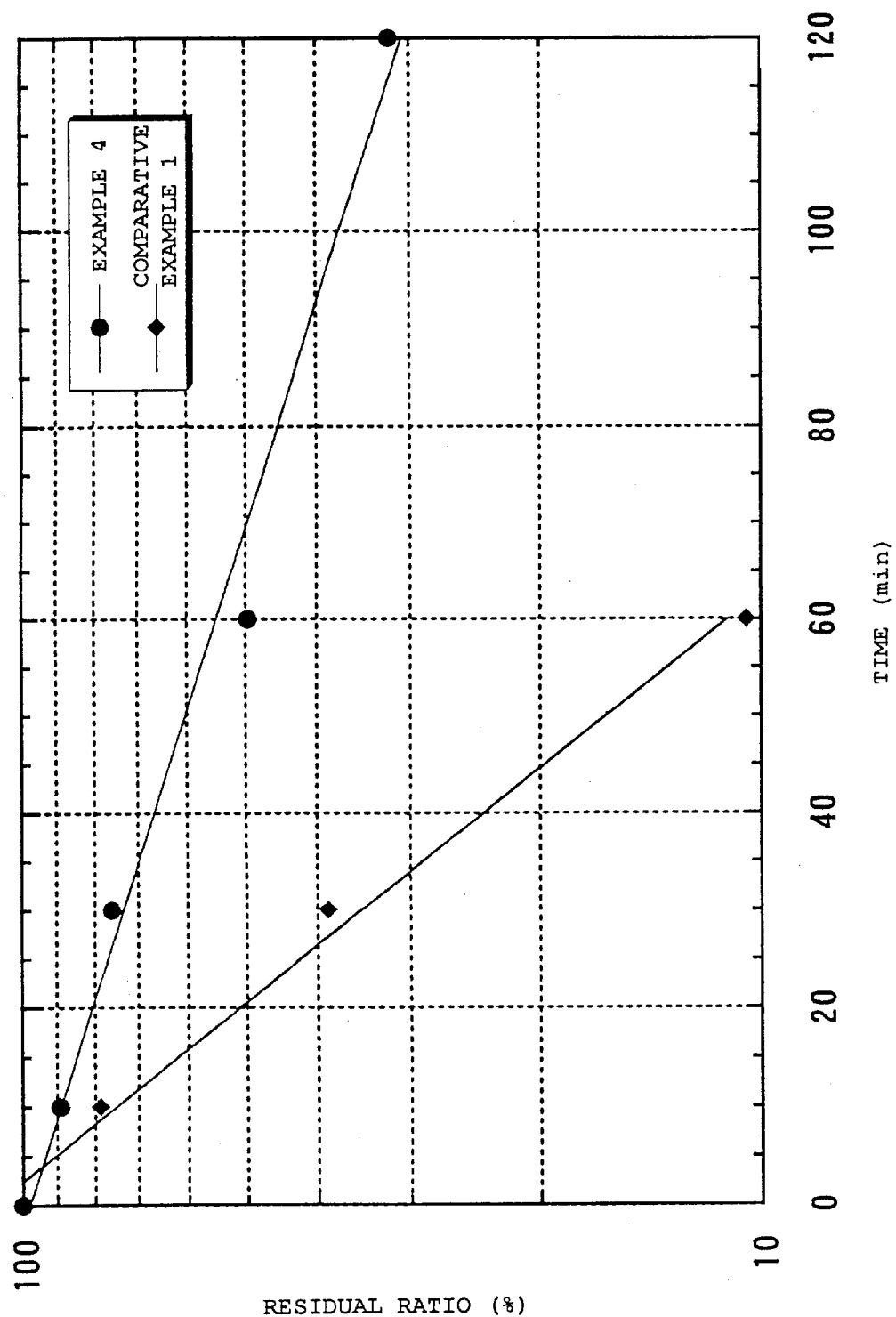
FIG. 2 is an experiment on swine liver esterase described in Example 19. The esterase concentration was 75 units/ml in Example 4 and 3.75 units/ml in Comparative Example 1.

(3) Since it was considered appropriate to assume that changes with time in the decomposition of the glutathione derivatives obtained in FIGS. 2–4 follow a linear disappearance curve, the decomposition rate constants and half lives were determined from these graphs, which are shown in Tables 2 and 3.

(4) The above results revealed that the glutathione derivatives comprising alkyl esters having 12 carbons or more have a relatively high physiological stability compared to the glutathione derivatives comprising alkyl esters having 10 carbons or less.

TABLE 2

| Compound | Decomposition rate constant by swine liver esterase ($10^{-4}$/unit/min) | Decomposition rate constant by rabbit liver esterase ($10^{-4}$/unit/min) |
| --- | --- | --- |
| Comparative Ex. 1 | 121 | — |
| Comparative Ex. 2 | 364 | 267 |
| Comparative Ex. 4 | 88.5 | 54.2 |
| Example 7 | 15.2 | 21.1 |
| Example 6 | 2.61 | 5.11 |
| Example 4 | 0.466 | 0.836 |
| Example 1 | 0.0901 | 0.300 |
| Example 2 | — | 0.523 |

TABLE 3

| Compound | Half life in rat plasma (min) | Half life in rabbit plasma (min) | Half life in human plasma (min) |
| --- | --- | --- | --- |
| Comparative Ex. 1 | 0.13 | 392 | 643 |
| Comparative Ex. 2 | 0.21 | 238 | 619 |
| Comparative Ex. 4 | — | 181 | — |
| Example 7 | — | 323 | — |
| Example 6 | — | 1084 | — |
| Example 4 | 154 | 1323 | 11086 |
| Example 1 | — | 24514 | — |

Example 20

Comparative Experiment of the HL-60 Cell Differentiation Induction and Growth-promoting Activity in Vitro of the Glutathione Derivative-1

Using the differentiation induction effect on the granulocytes or monocytes/macrophages obtained by culturing the human leukemia cell HL-60 in the presence of 9-cys-retinoic acid (9-cis-RA) or activated vitamin $D_3$ ($1\alpha, 25(OH)_2D_3$), and in the coexistence of the glutathione derivatives of Examples and the Comparative Examples of the present invention, the growth-promotion activity was tested.

(1) HL-60 cells used were purchased from the cell bank (Japanese Cancer Research Resource Bank, Cell No. JCRB0085). In accordance with a standard method, the lyophilized cell stocks that were thawed before the start of the experiment and subcultured were used.

Subculturing was carried out by centrifuging (1500 rpm, 5 minutes) the cells in suspension culture and recovering and by diluting it in a fresh culture liquid at a concentration of about 1/100 (1 to $2 \times 10^4$ cells/ml). As the culture liquid, an RPMI 1640 medium containing 10% fetal bovine serum was used.

(2) The cells subcultured in (1) were recovered by centrifugation (1500 rpm, 5 minutes), and were dispersed in the culture liquid at $2 \times 10^4$ cells/ml, which were plated on a 24-well culture plate at 1 ml/well. To this system were added the glutathione derivatives of Example 4, Example 11, Comparative Example 1 and Comparative Example 2 and a differentiation induction substance (9-cis-RA or $1\alpha, 25(OH)_2D_3$). Thus, 1 µl per well each of an ethanol solution of the differentiation induction substances 9-cis-RA and $1\alpha, 25(OH)_2D_3$ were added at $5 \times 10^{-6}$ M and $2 \times 10^{-6}$ M, respectively. Then, 1 µl per well each of ethanol solutions of the glutathione derivatives at $1 \times 10^{-4}$ M to $1 \times 10^{-2}$ M was added. As the solvent treatment for the control, 1 µl of ethanol per well was added in stead of the glutathione derivative, and as the single treatment of glutathione derivatives, 1 µl of ethanol per well was added in stead of the differentiation induction substance. After culturing at 37° C. and 5% $CO_2$ for 4 days, the cells were recovered by centrifugation (1500 rpm, 5 minutes).

(3) The measurement of a nitroblue tetrazolium (NBT) reducing activity which is often used for the evaluation of differentiation induction effects on monocytes/macrophages or granulocytic cells was carried out according to the following procedure. Thus, the cells recovered by centrifugation in (2) were suspended in a fresh culture medium, and then NBT was added thereto to 100 ng/ml and 12-O-tetradecanoyl phorbol-13-acetate to 100 nM. After incubating at 37° C. for 25 minutes, cytospin samples were prepared. After air drying, the cells were subjected to Kernechtrot stain, and 500 cells per sample were examined under alight microscope to determine the ratio of the NBT reduction activity-positive cells.

(4) The result of the experiment in which glutathione derivatives at $10^{-7}$ to $10^{-5}$ M were treated together with a differentiation induction substances is shown in Table 4. For a single treatment of each glutathione derivative up to $10^{-5}$ M, no increases in the NBT reducing activity was observed. In a combined treatment of a glutathione derivative and a differentiation induction substance, an enhanced ratio of the NBT reduction activity-positive cells relative to the single treatment with a differentiation induction substance was observed depending on the concentration of the glutathione derivative. There were no major differences observed in the strength of effects between the glutathione derivatives of Examples 4 and 11 and Comparative Examples 1, and 2.

TABLE 4

| Compound | Concentration (M) | Ratio of NBT reduction activity-positive cells (%) Differentiation induction substance | | |
| --- | --- | --- | --- | --- |
| | | Solvent control (EtOH) | $1\alpha, 25(OH)_2D_3$ ($2 \times 10^{-9}$ M) | 9-cis-RA ($5 \times 10^{-9}$ M) |
| Solvent control (EtOH) | 0 | 0.2 | 5.1 | 4.4 |
| Comparative Ex. 1 | $10^{-7}$ | 0.2 | 5.4 | 6.3 |
| | $10^{-6}$ | 0.2 | 7.6 | 10.1 |
| | $10^{-5}$ | 0.4 | 13.0 | 18.8 |
| Comparative Ex. 2 | $10^{-7}$ | 0.2 | 4.6 | 7.4 |
| | $10^{-6}$ | 0.4 | 9.3 | 15.2 |
| | $10^{-5}$ | 0.6 | 18.2 | 33.2 |
| Example 4 | $10^{-7}$ | 0.2 | 5.7 | 6.7 |
| | $10^{-6}$ | 0.2 | 10.3 | 10.4 |
| | $10^{-5}$ | 0.2 | 31.3 | 18.0 |
| Example 11 | $10^{-7}$ | 0.6 | 5.1 | 8.8 |
| | $10^{-6}$ | 0.2 | 4.8 | 11.2 |
| | $10^{-5}$ | 0.8 | 13.8 | 19.8 |

Example 21

Comparative Experiment of the HL-60 Cell Differentiation Induction and Growth-promoting Activity in Vitro of the Glutathione Derivative-2

In a manner similar to that in Example 20, the in vitro activity of the glutathione derivatives of Examples 4, 5, and 8, and Comparative Example 3 were compared.

(1) The differences from Example 20 were: First, since the glutathione derivatives of Examples and Comparative Examples used dimethyl sulfoxide (DMSO) as the solvent because of the solubility of the compounds, the system contained 0.1–0.3 (v/v)% DMSO instead of ethanol. Secondly, the concentration of 9-cis-RA was changed from $5 \times 10^{-9}$ M to $2 \times 10^{-9}$ M. This caused slight differences in the sensitivity in the test results of the glutathione derivative of Example 4. Furthermore, in Example 21, the differentiation induction on HL-60 cells into granulocytic cells in the coexistence of 9-cis-RA was only evaluated.

(2) The glutathione derivative of Example 4 exhibited an activity higher than that of Comparative Example 3. The glutathione derivatives of Examples 5 and 8 exhibited a differentiation induction activity of a similar degree to that of Comparative Example 3.

TABLE 5

| Compound | Concentration (M) | Ratio of NBT reduction activity-positive cells (%) Differentiation induction substance | |
| --- | --- | --- | --- |
| | | Solvent control (EtOH - 0.1%) | 9-cis-RA ($5 \times 10^{-9}$ M) |
| Solvent control (DMSO - 0.1 to 0.3%) | 0 | 0.3 | 2.9 |

TABLE 5-continued

| Compound | Concentration (M) | Ratio of NBT reduction activity-positive cells (%) Differentiation induction substance | |
|---|---|---|---|
| | | Solvent control (EtOH - 0.1%) | 9-cis-RA ($5 \times 10^{-9}$ M) |
| Comparative Ex. 3 | $10^{-8}$ | 0.7 | 3.1 |
| | $3 \times 10^{-8}$ | 0.5 | 2.8 |
| | $10^{-7}$ | 0.3 | 3.5 |
| | $3 \times 10^{-7}$ | 0.6 | 3.8 |
| | $10^{-6}$ | 0.3 | 6.1 |
| | $3 \times 10^{-6}$ | 0.6 | 17.1 |
| Example 4 | $10^{-8}$ | 0.6 | 2.5 |
| | $3 \times 10^{-8}$ | 0.7 | 3.1 |
| | $10^{-7}$ | 0.7 | 5.6 |
| | $3 \times 10^{-7}$ | 0.9 | 11.0 |
| | $10^{-6}$ | 0.3 | 21.2 |
| | $3 \times 10^{-6}$ | 0.6 | 29.9 |
| Example 5 | $10^{-8}$ | 0.3 | 2.5 |
| | $3 \times 10^{-8}$ | 0.7 | 2.1 |
| | $10^{-7}$ | 0.9 | 3.2 |
| | $3 \times 10^{-7}$ | 0.7 | 4.3 |
| | $10^{-6}$ | 0.3 | 6.5 |
| | $3 \times 10^{-6}$ | 0.2 | 11.2 |
| Example 8 | $10^{-8}$ | 0.5 | 2.9 |
| | $3 \times 10^{-8}$ | 0.4 | 3.2 |
| | $10^{-7}$ | 0.8 | 4.2 |
| | $3 \times 10^{-7}$ | 0.9 | 4.7 |
| | $10^{-6}$ | 0.8 | 8.8 |
| | $3 \times 10^{-6}$ | 0.7 | 16.9 |

Example 22

Comparison of the Effects of the Glutathione Derivatives of Comparative Examples 1 and 2 Combined With a Fat Emulsion and Example 18

The glutathione derivative combined with a fat emulsion was incubated with swine liver esterase to compare the resistance to decomposition.

(1) The glutathione derivatives of Comparative Examples 1 and 2 were mixed with a fat emulsion under the identical condition to that in Example 18. Thereupon, the concentration of the glutathione derivatives of Comparative Examples 1 and 2 in the fat emulsion were each adjusted to 1 mg/ml.

(2) The fat emulsion of the glutathione derivatives of Example 18, and Comparative Examples 1 and 2 was added to a reaction mixture of swine liver esterase at 15 (v/v)%. After incubation for a fixed time in a similar manner to that in Example 19, the content of the glutathione derivative was quantitated by HPLC. As the control experiment, an alcohol solution of the glutathione derivative of Example 4, Comparative Example 1 or 2 was added to the esterase reaction mixture together with physiological saline for adjustment of the total volume, and incubated similarly and analyzed by HPLC.

(3) Since a linear disappearance curve was observed as in Example 19, each decomposition rate constant was determined and was compared, which was summarized in Table 6.

(4) By mixing with the fat emulsion, the decomposition rate decreased for any of the glutathione derivatives, but the degree of reduction in the decomposition rate was more evident in the glutathione derivative of Example 4.

TABLE 6

| Compound | Decomposition rate constant in the presence of the fat emulsion (/unit/min) | Decomposition rate constant in the absence of the fat emulsion (/unit/min) | Ratio of decomposition rate constant (in the presence of the fat emulsion/ physiological saline) |
|---|---|---|---|
| Comparative Ex. 1 | $7.343 \times 10^{-3}$ | $1.206 \times 10^{-2}$ | 0.609 |
| Comparative Ex. 2 | $1.650 \times 10^{-2}$ | $3.638 \times 10^{-2}$ | 0.454 |
| Example 4 | $2.033 \times 10^{-5}$ | $1.100 \times 10^{-4}$ | 0.185 |

Example 23

Comparison of the Effects of the Glutathione Derivative of Comparative Example 1 Combined With a Fat Emulsion and Example 18

The glutathione derivative combined with a fat emulsion was dialyzed in an aqueous solution of glycerin to compare changes in the content of the glutathione derivative in the fat emulsion.

(1) The fat emulsion of Comparative Example 1 was prepared in a similar manner to that in Example 18. Thereupon, the concentration of the glutathione derivative in the fat emulsion was adjusted to 2 mg/ml.

(2) These fat emulsions (14 ml) were dialyzed in 1 liter of a 2.3 (w/v)% aqueous solution of glycerin. Dialysis was carried out at room temperature for 2 days with one change of the aqueous glycerin solution during the dialysis. All the fat emulsions after dialysis were about 15.6 ml. They were filtered by a 1.2 μm filter and the content of the glutathione derivative was measured.

(3) The content of the glutathione derivative of Example 18 (Example 4) was 85.7% of the initial feed as a value uncorrected for the volume increase due to dialysis, but the content in Comparative Example 1 was decreased to 14.0% after dialysis.

The result can be interpreted as follows: Thus, since the glutathione derivative of Example 4 is strongly included in the oil phase emulsion particles that can hardly pass through the dialysis membrane, the content in the fat emulsion after dialysis does not decrease much, whereas the glutathione derivative of Comparative Example 1 does not strongly interact with the emulsion particles, and thereby the content in the fat emulsion decreased due to the passage through the dialysis membrane.

(4) From the above result, it was thought that for the glutathione derivative of Example 4 that was administered together with the fat emulsion, a similar effect could be expected in vivo when the blood vessel was considered a dialysis membrane that is impervious to the oil phase emulsion particles.

Example 24

Comparison of Chances With Time in the Blood Levels of Glutathione Derivatives When the Fat Emulsion of Example 18 and the Aqueous Solution of Comparative Example 1 Were Intravenously Given to Mice The blood levels of the glutathione derivatives of Example 4 and Comparative Example 1 were compared in mice that are a species having a high esterase activity in the blood.

(1) Male 8-week old BDF1 mice were purchased from Nippon SLC and used for the experiment. Until 9-week old when they were subjected to the experiment, the animals were kept at a temperature of 24±2° C. and a humidity of 55±5% under the condition under which the animals had free access to the animal feed (MF, Oriental Yeast Co., Ltd.) and drinking water (well water treated with 0.4±0.2 ppm hypochlorous acid).

(2) The fat emulsion of Example 18 in which the concentration of the glutathione derivative of Example 4 was adjusted to 3 mg/ml and a saline solution of 2.5 (w/v)%-hydroxypropyl-β-cyclodextrin containing the glutathione derivative of Comparative Example 1 at 5 mg/ml were each administered to the tail vein of mice at a active ingredient concentration of 30 mg/kg-body weight and 50 mg/kg-body weight, respectively, and at 10 ml/kg-body weight as a liquid amount for both. After a fixed time, about 1 ml of blood was drawn from the heart of the animal under ethereal anesthesia (after drawing blood once, each mouse is sacrificed). The N number for each sample group at each time point was 2. After drawing, the blood was immediately cooled on ice and was centrifuged in the presence of sodium citrate to collect plasma. The plasma thus obtained was deproteinized with acetonitrile and then was analyzed by a C18 reverse phase high performance liquid chromatography using an aqueous solution of trifluoroacetic acid/acetonitrile system as the mobile phase to determine the concentration of glutathione derivative for each plasma.

(3) The results of plasma concentration of each glutathione derivative were summarized in Tables 7 and 8. The plasma level of the glutathione derivative of Comparative Example 1 was no greater than about a quantitation limit of 1 μg/ml already at 5 minutes after the administration. On the other hand, in mice that received the fat emulsion of Example 18, the glutathione derivative was detected in plasma until 2 hours after the administration.

(4) From the above results, it was found that the glutathione derivative disappeared very rapidly from the mouse plasma in the conventional technology of Comparative Example 1, whereas the glutathione derivative of Example 4 of the present invention remained in the plasma for a relatively long time.

TABLE 7

Plasma concentration after the administration of Example 18 (the glutathione derivative of Example 4)

| Time (min) | 5 | 10 | 15 | 30 | 60 | 120 | 180 |
|---|---|---|---|---|---|---|---|
| Individual 1 | 420.02 | 320.28 | 275.69 | 129.87 | 60.97 | 8.65 | Below detection limit |
| Individual 2 | 262.93 | 352.93 | 205.88 | 79.01 | 49.71 | 10.04 | Below detection limit |
| Mean | 341.47 | 336.61 | 240.79 | 104.44 | 55.34 | 9.34 | — |

At each time point of blood drawing, almost entire blood was taken from two mice and the mice were then sacrificed.

Units in the Table are μg/ml and the quantitation limit is about 1 μg/ml.

TABLE 8

Comparative Example 1 - Plasma concentration after the administration of the HPCD solution

| Time (min) | 5 | 15 | 60 |
|---|---|---|---|
| Individual 1 | Below quantitation limit | Below quantitation limit | Below quantitation limit |
| Individual 2 | Below quantitation limit | Below quantitation limit | Below quantitation limit |
| Mean | — | — | — |

At each time point of blood drawing, almost entire blood was taken from two mice and the mice were then sacrificed.

Units in the Table are μg/ml and the quantitation limit is about 1 μg/ml.

Example 25

Comparison of Changes With Time in the Concentration of the Glutathione Derivative in the Blood When the Fat Emulsion of a Glutathione Derivative Having a Long-chain Ester Having 12 Carbons or More and the Aqueous Solution of Comparative Example 1 and the Fat Emulsion of Comparative Example 2 Were intravenously Administered to Rabbits For the glutathione derivative of the present invention having a long-chain ester having 12 carbons or more and the glutathione derivatives of the conventional technology of Comparative Examples 1 and 2, kinetics in the blood were compared in rabbits that are a species having allow esterase activity in the blood.

(1) Male Japanese white rabbits, 12-week old or older, were purchased from Ichikawaya, and those rabbits that became 15-week old or older and whose body weight reached about 3 kg were used for the experiment. During the period up to the experiment, the animals were allowed free access to the animal feed and drinking water and were kept at a temperature of 24±2° C. and a humidity of 55±5%.

(2) The glutathione derivative having a long-chain ester of 12 carbons or more and the glutathione derivative of Comparative Example 2 were prepared at 20–200 mg/ml in a mixture of ethanol or ethanol:benzyl alcohol, which was mixed with the fat emulsion just prior to use, and was filtered with a 1.2 μm filter to obtain a liquid for intravenous administration. On the other hand, the glutathione derivative of Comparative Example 1 was dissolved in an aqueous solution of 6%-hydroxypropyl-β-cyclodextrin/5%-glucose at 15 mg/ml to obtain an administration liquid.

(3) The administration liquid of the glutathione derivative obtained in (2) at a dose of 2 ml/kg was rapidly infused into the left auricular vein of the rabbits under no anesthesia and under restraint at a rate of 1 ml/min. Each glutathione derivative was given to three or more rabbits. At 5, 10, 15, 30, 60, 120, and 240 minutes after the completion of the administration, 1 ml of the blood was drawn from the right auricular vein in the presence of heparin, which was immediately cooled on ice. Plasma was obtained by centrifuging the blood, 1–2 volume parts of acetonitrile was added to deproteinize the supernatant, which was filtered by a 0.5 μm filter. The supernatant of the filtrate was quantitated by HPLC.

(4) Changes with time in the plasma levels of each glutathione derivative were corrected by the dosage and shown in FIG. 5. From these data, pharmacokinetic analysis was carried out using the 2-compartment model to determine the distribution volume and clearance, which are shown in Table 9.

(5) From the above kinetic experiment on rabbits that is a species having a relatively low esterase activity in the blood, it was confirmed that the glutathione derivative having 12 carbons or more of the present invention has a tendency to be maintained continuously at high concentrations in an extremely marked manner as compared to the glutathione derivatives of the conventional technology of Comparative Examples 1 and 2.

TABLE 9

| Compound | Distribution volume per body weight of the central compartment (L/kg) | Clearance per body weight (L/kg/hr) |
| --- | --- | --- |
| Comparative Ex. 1 | 0.80 | 15.27 |
| Comparative Ex. 2 | 4.18 | 9.34 |
| Example 7 | 0.47 | 2.85 |
| Example 6 | 0.08 | 0.29 |
| Example 4 | 0.06 | 0.20 |
| Example 1 | 0.06 | 0.03 |
| Example 2 | 0.07 | 0.05 |

Example 26

Comparison of Pharmacological Effects of the Glutathione Derivatives of Example 4 and Comparative Example 1 in Rat Models of Suppressed Hematopoietic Function by 5-Fuluorouracil Administration Regarding the effect of promoting the recovery of neutrophil counts in rat models of suppressed hematopoietic function by 5-fuluorouracil administration, statistical significance was compared to the control group to compare the pharmaceutical composition containing Example 4 of the present invention as an active ingredient with the pharmaceutical composition of the conventional technology of Comparative Example 1 and granulocyte colony-stimulating factor (G-CSF).

(1) Animals used and the keeping condition: Male SD rats, 6-week old, purchased from Nippon SLC were used. The animal feed (manufactured by Oriental Yeast Co., Ltd.) and drinking water (well water treated with 0.4±0.2 ppm hypochlorous acid) were given ad libitum during the period of the experiment. The animals were housed in a hanging-type rat cage (manufactured by Nippon Cage K.K.) and kept at a temperature of 24±2° C. and a humidity of 55±5%.

(2) Creation of rat models of suppressed hematopoietic function by 5-FU administration; Creation of rat models of suppressed hematopoietic function by 5-FU (Kyowa Hakko Kogyo Co. Ltd.) administration was carried out based on the method of Akamatsu et al. (Yakuri to Chiryo(Pharmacology and Therapy), 18. (Suppl. 9), 317–356 (1990)). Thus, on the first day of the experiment, 5-FU at 50 mg/kg-body weight (dosage volume is 1 ml/kg-body weight) or the same amount of physiological saline (manufactured by Fuso Pharmaceuticals Industries, Ltd.) was intraperitoneally administered to the rats described in (1). On days 4, and 7–12, blood was drawn from the jugular vein and the EDTA-2K-treated blood was obtained. The blood was used to determine the neutrophil count using a general chemistry test instrument (Technicon H-1E, manufactured by Bayer-Sankyo K.K.) and the ratio of reticulocytes using a reticulocyte determination instrument (EPICS, XL-MCL, manufactured by Coulter K.K.). Blood was also drawn on day 1 of the experiment, and the values determined for the blood were used as the pre-administration values. The rats for which no reduction in the reticulocyte ratio was observed at a time point of day 4 were judged that no effects of 5-FU administration were recognized and were thereby excluded from the experiment.

In the physiological saline administration group, no changes in neutrophil count were observed throughout the experiment period, whereas in the 5-FU administration group there was a reduction in neutrophil count with the lowest value observed on day 8 of the experiment, and the neutrophil count was recovered to the value before 5-FU administration or higher on day 10 of the experiment or after. The above results confirmed that rat models of suppressed hematopoietic function can be created by a single intraperitoneal administration of 5-FU at 50 mg/kg-body weight.

(3) Evaluation of Example 4 and Comparative Example 1 in the above model; To the model described in (2), the glutathione derivative of Example 4 combined with the fat emulsion at 10 to 30 mg/kg-body weight/day or the glutathione derivative of Comparative Example 1 dissolved in a physiological saline containing 2.5% hydroxypropyl-β-cyclodextrin at 50 mg/kg-body weight/day was repeatedly administered into the tail vein for 9 days from day 2 to 10 of the experiment. The recombinant human G-CSF formulation (hereinafter referred to as G-CSF, manufactured by Chugai Pharmaceutical Co., Ltd.) as the positive control at 10 μg/kg-body weight/day and the empty fat emulsion as the negative control were administered in a similar manner. The dosage volume was 10 ml/kg-body weight/day for the negative control group, the Example 4—fat emulsion group, and the Comparative Example 1-HPCD solution group, and 1 ml/kg-body weight/day for the G-CSF group.

(4) The evaluation results of the effect of promoting the recovery of neutrophil counts in rat models of suppressed hematopoietic function by 5-FU administration are shown in FIGS. 6 and 7. In the G-CSF 10 μg/kg-body weight/day administration group, a statistically significant increase in neutrophil counts was observed relative to the negative control group on day 4 of the experiment. After it once decreased to a level almost equal to the negative control group on day 7 of the experiment, a statistically significant increase (a level of significance of 5%–0.1%) in neutrophil counts was again observed on a continuous basis on day 8 of the experiment and after. For the Example 4—fat emulsion group, there was a statistically significant increase (a level of significance of 5%–0.1%) in neutrophil counts in the 30 mg/kg-body weight/day administration group relative to the negative control group on a continuous basis from day 8 of the experiment, and the degree was almost equal to the G-CSF 10 μg/kg-body weight/day administration group. For the 20 mg/kg-body weight/day administration group, there was a constant increasing trend in neutrophil counts from day 8 of the experiment, and on days 9 to 11 of the experiment there was a statistically significant increase (a level of significance of 1% to 0.1%) relative to the negative control group. No changes were observed in the 10 mg/kg-body weight/day administration group compared to the negative control group. On the other hand, in the Comparative Example 1-HPCD solution group, even with the administration of 50 mg/kg-body weight/day, there was only a statistically significant increase (a level of significance of 5%) in neutrophil counts relative to the negative control group on day 12 of the experiment, and no changes were observed compared to the negative control group.

The above result indicated that in Comparative Example 1 the administration of up to 50 mg/kg-body weight/day together with the dissolution adjuvant HPCD did not cause any changes compared to the negative control group. On the other hand, the Example 4—fat emulsion administration group that received 20 mg/kg-body weight/day or higher was shown to have a dose-dependent effect of promoting the recovery of neutrophil counts in the rat models of suppressed hematopoietic function by 5-FU administration, and in the Example 4—fat emulsion administration group that received 30 mg/kg-body weight/day was shown to have an effect of promoting the recovery of neutrophil counts that is almost equal to that of the G-CSF 10 μg/kg-body weight/day administration group.

Example 27

Comparison of Pharmacological Effects of Examples 1, 4 and 7 in Rat Models of Suppressed Hematopoietic Function by 5-Fuluorouracil Administration (1) The animals used are the same as in Example 26. The keeping condition was a temperature of 23±2° C. and a humidity of 55±15%.

(2) The creation of the 5-FU administration model, the administration of test substances, and the blood collection schedule were carried out in a similar manner to Example 26. Hematological tests were carried out using the Toa multi-channel automatic cell counter K-4500 or Toa Sysmex CC-180A automatic cell counter, differential counts of white blood cells were carried out by May-Giemsa stain followed by microscopic examination, reticulocytes were counted by the Brecher method.

(3) Using the same schedule as in Example 26, the negative control group that only received the fat emulsion after 5-FU administration, the group that received the glutathione derivative of Example 4 at 30 mg/kg-body weight/day as a test substance together with the fat emulsion, the group that similarly received the glutathione derivative of Example 1 at 10 or 30 mg/kg-body weight/day, and the group that received the glutathione derivative of Example 7 at 30 or 60 mg/kg-body weight/day were studied. The rats in which reticulocytes did not decrease were excluded from the experiment by judging that no 5-FU effects were observed (one case).

(4) Changes in the ratio of segmented neutrophils during the study period are shown in FIG. 8. In the Example 4–30 mg/kg group as in Example 26, there was observed a tendency of promoting the recovery of segmented neutrophil counts (a level of significance of 5%–1% on days 9–12 of the experiment). In the glutathione derivative of Example 1, there was observed a tendency of promoting the recovery of segmented neutrophil counts in both of the 10 and 30 mg/kg groups (a level of significance 1% relative to the negative control group on days 8–12 and 7–12 of the experiment, respectively). Furthermore, in the glutathione derivative of Example 7 in the 30 mg/kg group, there were no changes relative to the negative control, whereas in the high dosage of 60 mg/kg group, there was observed a tendency of promoting the recovery of neutrophil counts (a level significance of 5% and 1% on days 11 and 12 of the experiment, respectively).

Example 28

Pharmacological Effects of the Glutathione Derivative of Example 4 in Normal Healthy Rats The effects of increasing neutrophil counts of the compound of Example 4 in normal healthy rats were studied.

(1) Male SD rats, 6-week old, purchased from Nippon SLC were used. The animal feed (MF, manufactured by Oriental Yeast Co., Ltd.) and drinking water (well water treated with 0.4±0.2 ppm hypochlorous acid) were given ad libitum during the period of the experiment. The animals were each housed in a hanging-type rat cage (manufactured by Nippon Cage K.K.) and kept at a temperature of 24±2° C. and a humidity of 55±5%.

(2) The glutathione derivative of Example 4 combined with the fat emulsion at 10, 20, or 30 mg/kg-body weight/day, and the fat emulsion alone as the negative control were each repeatedly administered into the tail vein for 6 days from day 1 to 6 of the experiment. Dosage was 10 ml/kg-body weight/day. From day 1 to 10 of the experiment, blood was drawn everyday from the jugular vein and the EDTA-2K-treated blood was obtained. Then the blood was used to determine the neutrophil counts using a general chemistry test instrument (Technicon H-1E, manufactured by Bayer-Sankyo K.K.).

Part of the negative control group on days 1, 7, and 10, and part of the Example 4—the fat emulsion 30 mg/kg-body weight/day administration group on days 3, 5, 7, and 10 of the experiment were bled to death from the abdominal aorta under anesthesia by the intraperitoneal administration of pentobarbital sodium. Then, the femoral bone marrow was harvested, smears were prepared therefrom using the wedge method, stained by the May-Giemsa stain, and examined under a microscope to determine the fractionation of nucleated bone marrow cells.

For part of the negative control group and the Example 4—fat emulsion 30 mg/kg-body weight/day administration group, plasma obtained form the EDTA-2K-treated blood on days 3, 5, and 7 of the experiment was used to determine plasma levels of interleukin 1β (hereinafter referred to as IL-1β) and tumor necrosis factor (hereinafter referred to as TNFα). For the determination, the rat IL-1β-ELISA system (manufactured by Amersham Pharmacia Biotek Co., Ltd.), the rat TNFα-ELISA system (manufactured by Amersham Pharmacia Biotek Co., Ltd.), and the BioRad microplate reader (MODEL550, Nippon BioRad laboratories, Co., Ltd.).

(3) The evaluation result of the effect of increasing neutrophil counts in normal healthy rats is shown in FIG. 9. For the Example 4—fat emulsion group, in the 30 mg/kg-body weight/day administration group a statistically significant increase in the neutrophil counts was observed relative to the negative control group on days 2, and 5–8 of the experiment (a level of significance of 5%–1%).

The results of effects on the bone marrow on days 1, 3, 5, 7, and 10 of the experiment are shown in FIGS. 10 and 11. When neutrophilic myelocytic cells are separately evaluated for the neutrophilic myelocytic cells (myeloblasts, promyelocytes, neutrophilic myelocytes, myelocytic dividing cells) having the dividing ability and for the neutrophilic myelocytic cells (neutrophilic metamyelocytes, stab neutrophils, segmented cells), the neutrophilic myelocytic cells having the dividing ability were increased in the Example 4—fat emulsion 30 mg/kg-body weight/day administration group on days 3 and 5 of the experiment, and returned to values almost equal to that of the negative control group on day 7 of the experiment. On the other hand, the neutrophilic myelocytic cells having no dividing ability were almost equal to the negative control group in the Example 4—fat emulsion 30 mg/kg-body weight/day administration group, but increases were observed on day 5, 7, and 10 of the experiment with the maximum value observed on day 7.

The evaluation result of the plasma levels of IL-1β and TNFα on days 3, 5, and 7 of the experiment are shown in FIGS. 12 and 13. No increases in IL-1β and TNFα were observed in the Example 4—fat emulsion 20 mg/kg-body weight/day administration group relative to the negative control group on any days of the experiment.

(4) From the above results, a pharmaceutical composition comprising the fat emulsion containing the glutathione derivative of Example 4 of the present invention was confirmed to have an activity of increasing neutrophil counts in the normal healthy rats as well, and hematopoiesis promoting activity was also observed in response to increases in neutrophil counts in the peripheral blood. Furthermore, it was found that changes in the inflammatory cytokines (IL-1β, TNFα) are not involved in the activity of increasing neutrophil counts.

Example 29

Comparison of Pharmacological Effects in Rabbit Models of Suppressed Hematopoietic Function by Cyclophosphamide Administration Regarding the effect of promoting the recovery of neutrophil counts in rabbit models of suppressed hematopoietic function by cyclophosphamide (hereinafter referred to as CP) administration, the pharmaceutical composition comprising the fat emulsion containing the glutathione derivative of Example 4 of the present invention and the pharmaceutical composition of the conventional technology of Comparative Example 1 were compared.

(1) Animals used and the keeping condition: Male Japanese white rabbits, 17-week old, (Kbl:JW) purchased from Kitayama Labes Co., Ltd. were used. The animal feed (LRC4, manufactured by Oriental Yeast Co., Ltd.) and drinking water (well water treated with 0.4±0.2 ppm hypochlorous acid) were given ad libitum during the period of the experiment. The animals were each housed in a hanging-type rat cage (manufactured by Nippon Cage K.K.) and kept at a temperature of 24±2° C. and a humidity of 55±5%.

(2) Creation of rabbit models of suppressed hematopoietic function by CP administration; CP (manufactured by Wako Pure Chemicals Industries, Ltd.) was intravenously administered at 60 mg/kg-body weight/day (dosage volume was 2 ml/kg-body weight) to rabbits described in (1) on day 1 and 2 of the experiment. On days 3–9, blood was drawn from the left auricular vein and the sodium heparin-treated blood was obtained. The blood was used to determine the neutrophil counts using a general chemistry test instrument (Technicon H-1E, manufactured by Bayer-Sankyo K.K.). Blood was also drawn before the administration on day 1 of the experiment, and the value determined for the blood was used as the pre-administration value. As a result, neutrophil counts were observed to be decreased with the lowest values observed on days 5–7, and they recovered to the pre-administration value or higher from day 8 of the experiment or after. The above results confirmed that rabbit models of suppressed hematopoietic function can be created by a 2-day administration Of CP at 60 mg/kg-body weight.

(3) Evaluation of the glutathione derivatives of Example 4 and Comparative Example 1 in the above model; To the model described in (2), the Example 4—fat emulsion at 20 mg/kg-body weight/day and the Comparative Example 1-hydroxypropyl-β-cyclodextrin (hereinafter referred to as HPCD) solution (the derivative of Comparative Example 1 was dissolved in an aqueous solution of 3% HPCD-2.2% glycerin) at 20 mg/kg-body weight/day were administered from day 3 to 7 of the experiment. The empty fat emulsion was administered to the negative control.

The evaluation results of the effect of promoting the recovery of neutrophil counts in rabbit models of suppressed hematopoietic function by CP administration are shown FIG. 14. In the Example 4—fat emulsion group, a statistically significant increase in neutrophil counts was continuously observed from days 6 to 8 of the experiment. On the other hand, no changes were observed in the Comparative Example 1-HPCD solution group compared to the negative control group.

The above result indicated that there were no changes observed when Comparative Example 1 combined with the dissolution adjuvant HPCD was administered compared to the negative control group. On the other hand, the Example 4—fat emulsion 20 mg/kg-body weight/day was shown to have the effect of promoting the recovery of neutrophil counts in rabbit models of suppressed hematopoietic function by CP administration.

When the stimulation of hematopoiesis promotion by pharmaceutical agents is reviewed here, it seems important to take the following into account. Naturally occurring hematopoiesis may be divided into the constitutive hematopoiesis at the steady state of the living body and the inductive hematopoiesis against various stimulations including infection and bleeding. In order to recover blood cell counts in the peripheral blood from the state of suppressed hematopoietic function in neutropenia or thrombocytopenia, it is necessary for inductive hematopoiesis to take place. In the case of hematopoietic factors derived from the living body such as G-CSF currently used in the clinical settings, differentiation and/or growth of hematopoietic stem cells and/or precursor cells present in the bone marrow are directly stimulated resulting in the production of mature blood cells. The hematopoietic mechanism which the present inventors consider to be clinically desirable is not what causes changes in various cytokines accompanied by inflammation together with infection and bleeding resulting in the secondary production of hematopoietic factors such as G-CSF, but what can directly induce the differentiation and/or growth of bone marrow stem cells or precursor cells in a similar manner to G-CSF. Thus, it appears necessary that low molecular weight hematopoietic substances that can possibly replace biologically active proteinaceous pharmaceuticals derived from the living body such as G-CSF need to have a property of exhibiting a hematopoiesis promoting effect by directly acting on bone marrow stem cells and/or precursor cells as well as a property of being capable of utilizing a mechanism that the pharmaceutical itself is administered in a form that enables efficient delivery to the bone marrow or the pharmaceutical efficiently reaches the bone marrow in the living body. Actually, G-CSF that acts on hematopoietic stem cells and granulocyte colony forming cells, because of being a macromolecule, has a small distribution volume (estimated by the present inventors from the experimental data in Sinryo to Sinnyaku (Diagnosis and New Drugs), Vol. 26(11), pp. 1660-, 1990) and therefore is considered to be effective in reaching the bone marrow. Although the specification of WO9640205 suggests the possibility that TER199 directly acts on the precursor cells in the bone marrow, no data have been presented that deny the possibility of being a secondary hematopoiesis promotion accompanied by inflammatory reactions nor are there any explicit description on the structures that can be efficiently delivered to the bone marrow and on the dosage form.

In fact, based on the above experiment by the present inventors, TER199 has an extremely short half life in the plasma of experimental animals such as mice and rats, and does not have a structure or form that can be efficiently delivered to the bone marrow. Thus, TER199 and its related compounds disclosed in the specification of WO9640205 cannot efficiently exhibit the effect of promoting hematopoiesis from a viewpoint of drug delivery.

What is claimed is:

1. A glutathione derivative or a salt thereof represented by the formula (I):

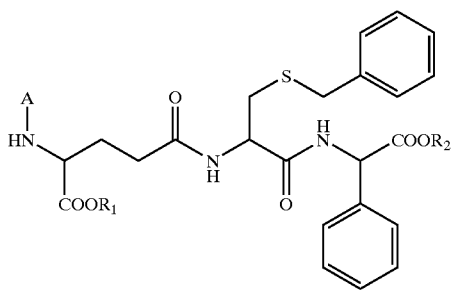

wherein A represents H or a C1–C20 acyl group;
$R_1$ represents a C1–C26 alkyl group or a C3–C26 alkenyl group; and
$R_2$ represents H, a C1–C26 alkyl group or a C3–C26 alkenyl group,
with the proviso that compounds are excluded in which $R_1$ is a C1–C10 alkyl group or a C3–C10 alkenyl group, and simultaneously $R_2$ is H, a C1–C10 alkyl group or a C3–C10 alkenyl group.

2. The glutathione derivative or a salt thereof according to claim 1 wherein $R_1$ represents a C1–C22 alkyl group or a C10–C22 alkenyl group.

3. The glutathione derivative or a salt thereof according to claim 1 wherein $R_1$ represents an ethyl group, a C10–C22 alkyl group or a C16–C20 alkenyl group.

4. The glutathione derivative or a salt thereof according to any of claims 1–3 wherein $R_2$ represents H, a C1–C22 alkyl group or a C3–C22 alkenyl group, with the proviso that compounds are excluded in which $R_1$ is a C1–C10 alkyl group or a C3–C10 alkenyl group, and simultaneously $R_2$ is H, a C1–C10 alkyl group or a C3–C10 alkenyl group.

5. The glutathione derivative or a salt thereof according to any of claims 1–3 wherein $R_2$ resents H, an ethyl group or a C10–C18 alkyl group.

6. The glutathione derivative or a salt thereof according to claim 1, wherein A resents H or an acetyl group.

7. The glutathione derivative or a salt thereof according to claim 1 or 6 wherein $R_1$ represents a C12–C22 alkyl group or a C18–C22 alkenyl group, and $R_2$ represents an ethyl group; or $R_1$ is an ethyl group, and $R_2$ is a C12–C18 alkyl group.

8. A pharmaceutical composition comprising a glutathione derivative or salt thereof according to claim 1 and a pharmaceutically acceptable carrier.

9. The pharmaceutical composition according to claim 8 wherein said pharmaceutical composition is colloidal.

10. The pharmaceutical composition according to claim 8 wherein said pharmaceutical composition is a fat emulsion, a liposome or a solid suspension.

11. The pharmaceutical composition according to claim 8 wherein said pharmaceutical composition is a fat emulsion.

12. A method of promoting hematopoiesis comprising administering a pharmaceutical composition according to claim 8 to a patient in need thereof for a time and under conditions effective to promote hematopoiesis.

13. The method according to claim 12, wherein said pharmaceutical composition is colloidal.

14. The method according to claim 12, wherein said pharmaceutical composition is a fat emulsion, a liposome or a solid suspension.

15. The method according to claim 12, wherein said pharmaceutical composition is a fat emulsion.

* * * * *